(12) United States Patent
Xia et al.

(10) Patent No.: US 11,112,393 B2
(45) Date of Patent: Sep. 7, 2021

(54) CHEMICAL INDICATOR AND METHOD OF USE

(71) Applicant: 3M INNOVATIVE PROPERTIES COMPANY, Saint Paul, MN (US)

(72) Inventors: Wensheng Xia, Woodbury, MN (US); Naiyong Jing, Saint Paul, MN (US); Matthew J. Bongers, Minneapolis, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 279 days.

(21) Appl. No.: 16/171,621

(22) Filed: Oct. 26, 2018

(65) Prior Publication Data

US 2019/0154646 A1   May 23, 2019

Related U.S. Application Data

(60) Provisional application No. 62/588,076, filed on Nov. 17, 2017.

(51) Int. Cl.
*G01N 31/22* (2006.01)
*G01N 21/17* (2006.01)
*C07C 409/04* (2006.01)

(52) U.S. Cl.
CPC ......... *G01N 31/228* (2013.01); *C07C 409/04* (2013.01); *G01N 21/17* (2013.01); *G01N 31/226* (2013.01); *G01N 2021/174* (2013.01)

(58) Field of Classification Search
CPC ......... F01N 2610/02; F01N 2610/1406; F01N 2610/144; F01N 2610/146; F01N 2610/1493; F01N 2900/1808; F01N 2900/1814; F01N 2900/1822; F01N 3/208; F01N 9/00; A61K 39/00; A61K 39/0208; B60L 13/06; C07C 409/04; C07K 14/315; C07K 16/1275; C07K 2317/21; F01L 2009/0405; F01L 2009/0486; F01L 9/04; F02D 13/0253; F02D 2041/001; F02D 2041/1419; F02D 2041/2027; F02D 2041/2055; F02D 2041/2058; F02D 2041/2079; F02D 41/1401; F02D 41/20;
(Continued)

(56) References Cited

U.S. PATENT DOCUMENTS 5,906,916 A   5/1999   Wu
6,329,207 B1  12/2001  Fricker
(Continued)

FOREIGN PATENT DOCUMENTS

WO   WO-2005111606 A2 * 11/2005   ............. C12Q 1/002
WO   WO-2015017591 A1 *  2/2015   ........... G01N 33/558
(Continued)

*Primary Examiner* — Jennifer Wecker
(74) *Attorney, Agent, or Firm* — Qiang Han

(57) ABSTRACT

A peracetic acid decontamination chemical indicator including a substrate and an indicator composition disposed thereon, where the indicator composition comprises a colorant that changes color when exposed to a peracetic acid solution but does not change color when exposed to a hydrogen peroxide solution, an acidified hydrogen peroxide solution, or an acetic acid solution, and where the indicator composition does not include a transition metal salt or a halogen source, and methods of using the chemical indicator.

16 Claims, 3 Drawing Sheets

(58) Field of Classification Search
CPC ............. G01N 2021/174; G01N 21/17; G01N 31/226; G01N 31/228; H01F 2007/185; H01F 2007/1866; H01F 2007/1894; H01F 7/1607; H01F 7/18; H01F 7/1844; H01H 47/325; H02K 41/03; H02N 15/00; H02P 25/032

See application file for complete search history.

(56) References Cited

U.S. PATENT DOCUMENTS

| | | | |
|---|---|---|---|
| 6,410,338 B1 | 6/2002 | Lippold | |
| 7,670,552 B2 | 3/2010 | Read | |
| 8,481,331 B2 | 7/2013 | Cregger | |
| 2003/0211618 A1* | 11/2003 | Patel | A61L 2/28 436/38 |
| 2006/0062688 A1* | 3/2006 | Lawrence | G01N 33/52 422/400 |
| 2007/0287182 A1* | 12/2007 | Morris | G01N 33/18 436/2 |
| 2009/0157024 A1* | 6/2009 | Song | G01N 21/80 604/361 |
| 2009/0325221 A1* | 12/2009 | Long | A61B 5/445 435/34 |
| 2013/0068155 A1* | 3/2013 | Patel | G01K 11/12 116/201 |
| 2015/0050745 A1 | 2/2015 | Karato | |
| 2015/0362435 A1* | 12/2015 | Hassan | G01M 3/12 422/429 |
| 2016/0033374 A1* | 2/2016 | Van Camp | G01N 1/34 73/865.8 |
| 2018/0094214 A1* | 4/2018 | Labib | C11D 11/0023 |

FOREIGN PATENT DOCUMENTS

| | | |
|---|---|---|
| WO | WO 2015-066760 | 5/2015 |
| WO | WO-2018017809 A1 * | 1/2018 ............. A01N 37/16 |

* cited by examiner

CHEMICAL INDICATOR AND METHOD OF USE

CROSS REFERENCE TO RELATED APPLICATIONS

This application claims priority from U.S. Provisional Application Ser. No. 62/588,076, filed Nov. 17, 2017, the disclosure of which is incorporated by reference in its entirety herein.

TECHNICAL FIELD

The present disclosure generally relates to chemical indicators, especially chemical indicators for the monitoring of decontamination processes including peracetic acid.

BACKGROUND

Reusable medical devices, such as reusable endoscopes, are commonly used in medical procedures. These medical procedures may expose the reusable medical devices to biological soil, such as blood, fecal matter, cellular matter from various tissue, and the like, which may harbor pathogens, e.g., bacteria, viruses. These pathogens can pass from one patient to another if the reusable medical device is not sufficiently disinfected prior to its use in subsequent medical procedures, and improperly reprocessed endoscopes have been linked to outbreaks of bacterial infection.

Because of the potentially harmful consequences of improper endoscope reprocessing, it is desirable to monitor decontamination procedures to ensure that endoscopes are reprocessed properly. Such monitoring may be accomplished, for example, by employing a chemical indicator ("CI") and/or biological indicator ("BI"). One type of CI, a "process indicator" can provide an indication e.g., a color change, that informs the endoscope user that the medical devices were processed, but not necessarily whether the appropriate conditions for sterilization or high-level disinfection were achieved. Another type of CI, an "integrating indicator" or "integrator," refers to a CI that can react to more than one process parameter, e.g., concentration of a sterilant, contact time of a sterilant, required minimum temperature of a process, over a specified range of high-level disinfection or sterilization cycles. An integrator may provide an indication e.g., a color change, that informs the endoscope user not only that the medical devices were processed, but that one or more process parameters met or exceeded minimum levels required for effective decontamination. The performance of integrators may be correlated to the performance of a BI under its labeled conditions for use, and may be used in place of the BI in many applications, thereby potentially reducing the overall cost of decontamination processing.

SUMMARY

In one aspect, provided is a peracetic acid decontamination chemical indicator comprising a substrate and an indicator composition disposed thereon, wherein the indicator composition comprises a colorant that changes color when exposed to a peracetic acid solution but does not change color when exposed to a hydrogen peroxide solution, an acidified hydrogen peroxide solution, or an acetic acid solution, and wherein the indicator composition does not include a transition metal salt or a halogen source.

In another aspect, provided is a method of monitoring a peracetic acid decontamination process, the method comprising exposing an article to be disinfected and the peracetic acid decontamination indicator of the present disclosure to a sterilant comprising peracetic acid during a decontamination process, where a predetermined decontamination exposure criterion exists for contacting the article with the sterilant, measuring a color change of the exposed peracetic acid decontamination indicator, where the color change is predictive of the predetermined disinfectant exposure criterion, and determining whether the predetermined disinfectant exposure criterion has been achieved.

Features and advantages of the present disclosure will be further understood upon consideration of the detailed description as well as the appended claims.

Figure 1:
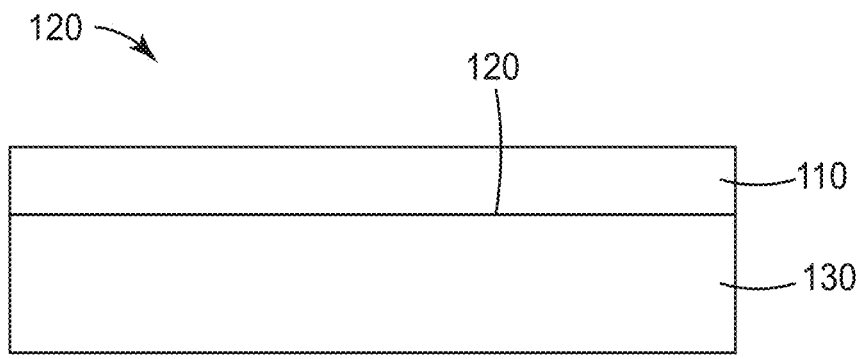
FIG. 1 shows an embodiment of a chemical indicator of the present disclosure.

Repeated use of reference characters in the specification and drawings is intended to represent the same or analogous features or elements of the disclosure. It should be understood that numerous other modifications and embodiments can be devised by those skilled in the art, which fall within the scope and spirit of the principles of the disclosure. The figures may not be drawn to scale.

DETAILED DESCRIPTION

It is known that the reuse of endoscopes in hospitals can lead to potentially life-threatening infections in patients and that the proper reprocessing, i.e., high-level disinfection, of endoscopes is critical to ensuring patient safety. Peracetic acid ("PAA") solution, a clear, colorless liquid that may be prepared by combining aqueous hydrogen peroxide and acetic acid, is a high-level disinfectant ("HLD"), used for endoscope reprocessing in automated endoscope reprocessing ("AER") machines. Due to its environmental friendliness and low toxicity, PAA has been gaining attention from healthcare professional and may be used in preference to other available HLDs. AER machines using a PAA sterilant may include some process monitoring features, but may not deliver a complete picture of the endoscope decontamination process, and this incomplete picture may lead to uncertainty that endoscope decontamination processes have provided effective high-level disinfection. It is therefore desirable to provide healthcare professionals with an integrator device for use with AER machines employing PAA as the sterilant that can include monitoring capabilities for some of the most critical parameters of endoscope reprocessing such as, for example, processing temperature, sterilant concentration, decontamination time, and sterilant flow in the AER machine, so that process quality can be evaluated.

The terms "colorant" and "indicator dye" are used interchangeably herein, and generally refer to an organic molecule that shows visually by a color change whether a particular material, e.g., peracetic acid, hydrogen peroxide, hydronium ion, is present in a solution. Unless specified otherwise, colorants of the present disclosure are used as delivered from the vendor and are not "pre-reacted", e.g., treated with an oxidizing agent, treated with a reducing agent, prior to incorporation into a chemical indicator and use in a decontamination process, such as, for example, the pre-reacted colorants disclosed in U.S. Pat. No. 8,481,331 (Cregger et al.).

The terms "decontamination" and "decontamination process" as used herein means a process through which instruments and/or supplies may be cleaned, and refer to both sterilization and high-level disinfection processes.

The term "inhibitor" as used herein refers to a chemical which inhibits a known concentration of peracetic acid, thus preventing a colorant from indicating the presence of PAA below that concentration as disclosed in U.S. Pat. No. 6,329,207 (Fricker et al.).

The terms "sterilant" and "sterilant liquid" as used herein refer to a solution e.g. peracetic acid solution, that may be used in a decontamination process such as, for example, a sterilization process and/or a high-level disinfection process.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the term "coupled" and variations thereof are used broadly and encompass both direct and indirect couplings. It is to be understood that other embodiments may be utilized, and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

In one aspect, provided is a chemical indicator for the monitoring of decontamination processes including peracetic acid ("PAA"), where the chemical indicator includes a substrate and an indicator composition disposed thereon.

Substrate

Substrates useful in embodiments of the present disclosure are stable and unreactive under the conditions (e.g., temperature, solvent, sterilant) typically associated with a given decontamination process.

Substrates useful in embodiments of the present disclosure may comprise, for example, a glass, an organic polymer, a silica particle, a metal, a ceramic, a fabric, a paper, and combinations thereof. Substrates suitable for use in embodiments of the present disclosure may be transparent or opaque. In some embodiments, the substrate may comprise a polymer film, a membrane, or a paper that is adapted for use as an indicator in a decontamination device, such as, for example, an automated endoscope reprocessing apparatus.

In some embodiments, the substrate may include a transparent polymer film such as, for example, a polyethylene terephthalate, a polymethyl methacrylate, a polycarbonate, and combinations thereof. In some embodiments, the substrate may comprise a membrane such as, for example, polyethersulfone membrane and/or a nylon membrane. In some embodiments, the substrate may comprise a nylon membrane selected from the group consisting of an uncharged nylon membrane, a positively charged nylon membrane, a negatively charged nylon membrane, and combinations thereof. In some embodiments, the substrate may comprise a silica particle selected from the group consisting of an uncharged silica particle, a positively charged silica particle, a negatively charged silica particle, and combinations thereof. In some embodiments, the substrate may be selected from the group consisting of a nylon membrane, a silica particle, a polymer film, and combinations thereof. In some embodiments, the substrate may comprise a silica particle affixed to a pressure sensitive adhesive-coated polymer film. In some embodiments, the silica particle may be functionalized silica particle, such as, for example, a trimethylammonium functionalized silica particle, with a counterion, such as, for example, a carbonate counterion or a chloride counterion.

Indicator Composition

An indicator composition of the present disclosure includes a colorant. Preferably the colorant is not a pre-reacted colorant. Colorants suitable for use in embodiments of the present disclosure include indicator dyes that change color, e.g., colorless to orange, yellow to colorless, colorless to red, when exposed to a peracetic acid solution, e.g., an at least 0.055 wt % peracetic acid solution, but do not change color when exposed to a hydrogen peroxide solution, e.g., an at least 2 wt % hydrogen peroxide solution, an acidified hydrogen peroxide solution, e.g., an at least 2 wt % hydrogen peroxide solution acidified with 1N hydrochloric acid, or an acetic acid solution, e.g., 0.1N acetic acid solution.

In some embodiments, suitable colorants may include an organic moiety selected from the group consisting of an azido, a benzidine, a benzothiazole, a benzoxazole, an indole, a pyrazole, a pyridine, a quinoline, a stilbene, a styrene, a sugar (e.g., fructose, galactose, glucose, mannose, xylopyranose), and combinations thereof. In some embodiments, the colorant does not include an organic moiety selected from the group consisting of a naphthalene moiety, an anthraquinone moiety, and combinations thereof. In some embodiments, the colorant does not include an organic moiety selected from the group consisting of a naphthalene moiety, an anthraquinone moiety, an azine moiety, an oxazine moiety, a thiazine moiety, and combinations thereof.

Specific examples of colorants useful in embodiments of the present disclosure include 5-bromo-4-chloro-3-indolyl beta-D-galactopyranoside, 4,4'-diamino-2,2'-stilbenedisulfonic acid, 4-aminoantipyrine, quinaldine red, 2-[4-(dimethylamino)styryl]-1-methylpyridinium iodide, 2,2'-azino-bis(3-ethylbenzothiazoline-6-sulfonic acid) diammonium salt, 3,3'-diaminobenzidine, merocyanine 540, azidoaniline, trans-4-[4-(dimethylamino)styryl]-1-methylpyridinium iodide, tetramethylbenzidine hydrochloride, and combinations thereof.

Surprisingly, indicator compositions of the present disclosure do not require the presence of an additional reagent, such as, for example, a halogen source, e.g., a halogen salt, as disclosed in U.S. Pat. No. 6,706,537, a transition metal salt, e.g., cobalt acetate, ferrous sulfate, as disclosed in U.S. Pat. No. 7,670,552 (Read), or an inhibitor which inhibits a known concentration of PAA, e.g., sodium thiosulfate, ceric ammonium sulfate, as disclosed in U.S. Pat. No. 6,329,207 (Fricker et al.) to carry out their desired function in a chemical indicator for monitoring of a PAA decontamination process. Therefore, in another aspect, the present disclosure provides a chemical indicator consisting essentially of a substrate and a colorant. Suitable substrates and colorants are described above.

The indicator composition is generally formulated in the form of a dispersion or solution in water or an organic solvent. The indicator composition includes at least one colorant as described above.

In some embodiments, particularly in embodiments where the substrate has a neutral charge, such as, for example, a polyethylene terephthalate film or an uncharged nylon membrane, to facilitate coating of the indicator composition on the substrate, the indicator composition may further include a polymeric binder. In embodiments where a liquid vehicle (e.g., water), is present during preparation of the indicator composition, the additional polymeric binder is preferably dispersible or soluble in the liquid vehicle. Exemplary additional polymeric binders include water-soluble polymers such as, for example, polyvinyl alcohol, hydroxyethyl cellulose, hydroxypropyl cellulose, and polymer latexes (e.g., polyurethane latexes, acrylic latexes, vinyl acetate latexes, and combinations thereof). Suitable polymeric binders include film-forming polymeric binders, which may be provided, for example, as a latex. In some preferred embodiments, the latex is added to the indicator composition prior to depositing the mixture on a substrate. Suitable film-forming polymers can include acrylics (e.g., polybutyl acrylate and polymethyl methacrylate), ethylene-vinyl acetate copolymers (and partially or completely hydrolyzed versions thereof), polyvinyl alcohols, polyurethanes, polyamides, polyvinyl chloride, polystyrenes, polyesters, polycarbonates, natural and synthetic rubbers, and combinations thereof. The film-forming polymeric binder may be self-crosslinkable and/or may be used in conjunction with a crosslinking agent.

If present, the inert film-forming polymeric binder may be present in an amount of up to 99 percent by weight, from 5 to 99 percent by weight, or from 40 to 80 percent by weight, based on the combined total weight of the indicator composition including any solvent. For indicator compositions in which the solvent has been removed, the inert film-forming polymeric binder may be present in an amount of up to 60 percent by weight, from 10 to 60 percent by weight, or from 20 to 40 percent by weight, based on the combined total weight of the solid components of the indicator composition.

In another aspect, the present disclosure provides a chemical indicator consisting essentially of a colorant, a substrate, and a binder. Suitable colorants, substrates, and binders are described above.

In some embodiments, the indicator composition may further include a base. Bases suitable for use in embodiments of the present disclosure may include an inorganic base (e.g., aqueous ammonia, hydroxides of Group I metals and Group II metals), an organic base (e.g., triethylamine, thiethanolamine, trimethylamine), an amine-derivatized silane (e.g., 3-aminopropyltrimethoxysilane, N-[3-(trimethoxysilyl)propyl]ethylenediamine, N-[3-(trimethoxysilyl)propyl]aniline, trimethoxy[3-(methylamino)propyl]silane), and combinations thereof.

If present, the base may be present in an amount of up to 20 percent by weight, from 0.5 to 20 percent by weight, or from 0.5 to 5 percent by weight, based on the combined total weight of the indicator composition including any solvent.

The indicator composition may optionally further comprise various additives such as, for example, rheology modifying agents, inert color enhancement agents (e.g., titanium oxide), UV stabilizers, an antioxidant agent to control the reaction speed as a delaying agent, wetting and leveling agents, and combinations thereof.

Indicator compositions of the present disclosure can be prepared by suspending a colorant in a suitable solvent (e.g., water, dimethyl formamide) to provide a colorant solution, optionally with heating or cooling. In some embodiments, one or more optional bases, described above, may be added to the colorant solution. In some embodiments, one or more optional binders (e.g., a polymer latex), described above, may be added to the colorant solution. In some embodiments, one or more optional crosslinking agents (e.g., an aziridine crosslinker) may be added to the colorant solution.

The indicator composition can be applied to the substrate by a suitable method known to those of ordinary skill in the relevant arts including, for example, spin coating, dip coating, spraying, brushing, roll coating, gravure coating, curtain coating, knife coating, and slot coating. In some embodiments, heating may be advantageously applied after coating (e.g., to facilitate crosslinking and/or remove any optional solvent). In some embodiments, the colorant may be adsorbed on a functionalized silica particle, followed by disposition of the silica particles onto the surface of a pressure-sensitive adhesive tape.

An embodiment of a chemical indicator of the present disclosure is shown in FIG. 1. Referring now to FIG. 1, exemplary chemical indicator 100 comprises an indicator composition layer 110 (i.e., an indicator composition according to the present disclosure) disposed on surface 120 of substrate 130. Layer 110 may have any suitable thickness, commonly from. In some embodiments, the thickness of the indicator composition layer is more than 4 microns, more than 5 microns, more than 6 microns, more than 7 microns, or more than 8 microns.

Desirably, any color change of a chemical indicator that occurs due to exposure of the chemical indicator to a decontamination process is stable i.e., does not change by more than 1%, more than 2%, more than 3%, more than 4%, or more than 5% for a period of time after such exposure concludes that is sufficient to allow an operator to measure the color change. In some embodiments, the color change of the chemical indicator associated with exposure to a PAA sterilant is stable for at least one minute, at least 5 minutes, at least 10 minutes, at least 20 minutes, at least 30 minutes, at least 45 minutes, or at least one hour.

Method of Using the Chemical Indicator

Chemical indicators of the present disclosure may be used to monitor decontamination processes, particularly decontamination processes including peracetic acid ("PAA") solutions such as, for example, automated endoscope reprocessing.

During a decontamination process, as a result of contact of the chemical indicator with PAA, the indicator composition may change color and/or emit light (e.g., fluoresce), which can be determined visually and/or spectrally (e.g., by reflectance, transmission, and/or fluorescence spectroscopy), thereby providing an indication of the presence of PAA. Furthermore, the extent to which the indicator composition changes color, e.g., the change in the magnitude of percent reflectance at a given wavelength, may be used to determine not only the presence of PAA, but whether a predetermined decontamination exposure criterion, such as, for example, the concentration of PAA in a sterilant, the decontamination temperature, the decontamination time, the sterilant flow, and combinations thereof, was achieved during a decontamination process. The predetermined disinfectant exposure criterion may correspond to an industry and/or governmental standard and/or guidelines or protocol for decontamination of the medical device, or the medical device manufacturer's specific decontamination procedure.

Provided is a method of monitoring a peracetic acid decontamination process. The method comprises exposing an article to be disinfected, e.g., an endoscope, and a peracetic acid decontamination indicator prepared as described above to a sterilant comprising peracetic acid during a decontamination process, wherein a predetermined disinfectant exposure criterion exists for contacting the article with the sterilant and detecting a color change and/or a fluorescence change of the decontamination indicator after exposure to the sterilant liquid comprising peracetic acid, wherein the color change is predictive of the predetermined disinfectant exposure criterion, and determining whether the predetermined disinfectant exposure criterion has been achieved.

In some embodiments, the color change of the decontamination indicator upon exposure to the sterilant liquid is dependent upon a decontamination process condition selected from the group consisting of concentration of peracetic acid in the sterilant liquid, exposure temperature, exposure time, the rate of sterilant liquid flow across the decontamination indicator, and combinations thereof.

A predetermined decontamination exposure criterion for a given decontamination condition may vary depending on the type of decontamination sterilant and decontamination device employed. In some embodiments, the concentration of peracetic acid in the sterilant liquid is at least 550 ppm, at least 850 ppm, at least 1,000 ppm, at least 1,500 ppm, or at least 2,000 ppm during the decontamination process. In some embodiments, the temperature of the sterilant liquid is 20° C.-50° C., 25° C.-48° C., or 30° C.-46° C. during the decontamination process. In some embodiments, exposure time of the decontamination indicator to the sterilant liquid is at least 1 minute, at least 2 minutes, at least 3 minutes, at least 4 minutes, at least 5 minutes, at least 6 minutes, at least 7 minutes, at least 8 minutes, at least 9 minutes, or at least 10 minutes. In some embodiments, the rate of sterilant liquid flow across the decontamination indicator is at least 200 mL per minute, at least 300 mL per minute, at least 400 mL per minute, at least 500 mL per minute, at least 600 mL per minute, or at least 700 mL per minute.

To determine whether a decontamination process has been effective, i.e., whether one or more predetermined decontamination exposure criteria has been achieved, a color change and/or fluorescence of a decontamination indicator of the present disclosure may be measured. In some embodiments, detecting the color change of the decontamination indicator comprises detecting a change in percent optical reflectance and or fluorescence of the decontamination indicator at 375 nm-800 nm, 400 nm-500 nm, 450 nm, or at more than one wavelength (e.g., 450 nm and 550 nm). The resulting reflectance measurement and/or the ratio of reflectance measurements at two wavelengths (e.g., 450 nm and 550 nm) may then be compared to a reflectance measurement and/or ratio of reflectance measurements for a decontamination indicator wherein the color change is predictive of the predetermined disinfectant exposure criterion. A reflectance value and/or the ratio of reflectance values at two wavelengths at or below a value corresponding to the predetermined decontamination exposure criterion would indicate a successful decontamination process, whereas a reflectance value and/or the ratio of reflectance values at two wavelengths above a value corresponding to the predetermined decontamination exposure criterion would indicate an unsuccessful decontamination process.

A decontamination indicator of the present may be prepared and used as described above. It is also possible to incorporate a decontamination indicator of the present disclosure into a device, such as, for example, a process challenge device as described in International Publication No. WO/2016/164329 (Bommarito).

EXAMPLES

Unless otherwise noted, all parts, percentages, ratios, etc. in the Examples and the rest of the specification are by weight.

Materials

| Material | Abbreviation | Supplier |
|---|---|---|
| (2,2'-Azino-bis(3-ethylbenzothiazoline-6-sulfonic acid) diammonium salt | ABTS | Sigma Aldrich (St Louis, MO) |
| 3,3'-Diaminobenzidine | | Sigma Aldrich (St Louis, MO) |
| Merocyanine 540 | | Sigma Aldrich (St Louis, MO) |
| Azidoaniline | | Sigma Aldrich (St Louis, MO) |
| trans-4-[4-(Dimethylamino)styryl]-1-methylpyridinium iodide | | Sigma Aldrich (St Louis, MO) |
| Tetramethylbenzidine hydrochloride | | Sigma Aldrich (St Louis, MO) |
| 5-Bromo-4-chloro-3-indolyl beta-D-Galactopyranoside | | Sigma Aldrich (St Louis, MO) |
| 4,4'-Diamino-2,2'-stilbenedisulfonic acid | | Sigma Aldrich (St Louis, MO) |
| 4-Aminoantipyrine | | Sigma Aldrich (St Louis, MO) |
| Quinaldine red | | Sigma Aldrich (St Louis, MO) |
| 2-[4-(Dimethylamino)styryl]-1-methylpyridinium iodide | | Sigma Aldrich (St Louis, MO) |
| 3-Aminopropyltrimethoxysilane | APS | Sigma Aldrich (St Louis, MO) |
| Dimethylformide | DMF | Sigma Aldrich (St Louis, MO) |
| 30% Hydrogen peroxide solution | | Sigma Aldrich (St Louis, MO) |
| 4,4'-Diaminostilbene dihydrochloride | DABA | Sigma Aldrich (St Louis, MO) |
| Diaminobenzenesulfonic acid | DABSA | Sigma Aldrich (St Louis, MO) |
| 4,4'-Diamino-2,2'-stilbenedisulfonic acid | DSSA | Tokyo Chemical Industry (TCI) |
| N-[3-(Trimethoxysilyl)propyl]ethylenediamine | AEAPS | Sigma Aldrich (St Louis, MO) |
| BONDTHANE UD-420 | UD420 | Bond Polymers International (Seabrook NH) |
| PZ-28 Aziridine crosslinker | PZ-28 | PolyAziridine LLC (Medford, NJ) |

-continued

| Material | Abbreviation | Supplier |
| --- | --- | --- |
| NEOCRYL A1049 | A1049 | DSM USA (Parsippany, NJ) |
| NEOCRYL A612 | A612 | DSM USA (Parsippany, NJ) |
| Colloidal silica 2326 | 2326 | Nalco (Naperville, IL) |
| Colloidal silica 2327 | 2327 | Nalco (Naperville, IL) |
| 3-(Trimethylammonium)propyl-functionalized silica gel, carbonate | | Sigma Aldrich (St Louis, MO) |
| SILIABOND TMA Chloride | | SiliCycle (Quebec City, Canada) |
| SILIABOND Carbonate | | SiliCycle (Quebec City, Canada) |
| Ammonia (30% aqueous) | | EMD Millipore (Billerica, MA) |
| Triethylamine | TEA | EMD Millipore (Billerica, MA) |
| NEOREZ R-966 | R966 | DSM USA (Parsippany, NJ) |
| NEOREZ R-600 | R600 | DSM USA (Parsippany, NJ) |
| NEOREZ R-9603 | | DSM USA (Parsippany, NJ) |
| NEOREZ R-650 | | DSM USA (Parsippany, NJ) |
| NEOREZ R-4000 | | DSM USA (Parsippany, NJ) |
| INCOREZ cs8057 | | Incorez (Preston, Lancashire, UK) |
| RAPICIDE PA | | Medivators, Inc. (Minneapolis, MN) |
| ACECIDE-C | | OLYMPUS AMERICA (Center Valley, PA) |
| NM87701080AM Ammonium Nylon Membrane | | 3M Purification, Inc. (Meriden, CT) |
| NM87701080ZN Nylon Membrane | | 3M Purification, Inc. (Meriden, CT) |
| Magma nylon - cationically modified nylon | | 3M Purification, Inc. (Meriden, CT) |
| Polyethylene terephthalate film, 5 mil, primed with Rhoplex on coating side | PET | 3M FMSCO (St. Paul, MN) |
| Silicon Pressure Sensitive Adhesive-coated tape 9795R | PSA | 3M (St. Paul, MN) |
| INTERCEPT detergent | | Medivators, Inc. (Minneapolis, MN) |
| TEGO Twin 4200 | | Evonik Corporations (Parsippany, NJ) |

Example 1

As provided in Table 1, each dye (200 mg) was dissolved in 10 mL of water, 0.1N NaOH, or DMF to make a stock solution. A working RAPICIDE PA solution ("PAA") was prepared according to the manufacturer's instruction by combining one part of Part A and one part of Part B in 48 parts deionized water (approximately 1,100 ppm PAA). An acidic 2% hydrogen peroxide solution was prepared by diluting 30% hydrogen peroxide in deionized water acidified with two drops of 1N HCl. To 10 mL of the three different test solutions, namely, Rapicide PA solution, acidic water solution (two drops of 1N HCl solution added to 10 mL water) and acidic 2% hydrogen peroxide solution (two drops of 1N HCl solution added to 10 mL to keep solution acidic), 100 μL of each dye solution was added. The reaction was allowed to proceed for 10 minutes and then the color of each reaction solution was recorded. Table 1 shows the results of dye screening after 10 minutes reaction for various dyes.

TABLE 1

Dye Screening Results

| Indicator Dye name | Solvent/Dye Color in Solution | Color of Dye in PAA Solution | Color of Dye in acidic 2% $H_2O_2$ Solution | Color of Dye in Acidic Solution |
| --- | --- | --- | --- | --- |
| 5-Bromo-4-chloro-3-indolyl beta-D-galactopyranoside | DMF/Colorless | Yellow | Colorless | Colorless |
| 4,4'-Diamino-2,2'-stilbenedisulfonic acid (DSSA) | 0.1N NaOH/Colorless | Orange to red | Colorless | Colorless |
| 4-Aminoantipyrine | Water/Colorless | Red | Colorless | Colorless |
| Quinaldine red | DMF/Red | Colorless | Red | Red |
| 2-[4-(Dimethylamino)styryl]-1-methylpyridinium iodide | DMF/Yellow | Colorless | Yellow | Yellow |
| 2,2'-Azino-bis(3-ethylbenzothiazoline-6-sulfonic acid) diammonium salt (ABTS) | Water/Colorless | Green | Colorless | Colorless |
| 3,3'-Diaminobenzidine | DMF/Colorless | Red | Colorless | Colorless |
| Merocyanine 540 | Water/Red | Yellow | Red | Red |
| Azidoaniline | Water/Colorless | Yellow | Colorless | Colorless |
| trans-4-[4-(Dimethylamino)styryl]-1-methylpyridinium iodide | DMF/Orange | Colorless | Orange | Orange |
| Tetramethylbenzidine hydrochloride | Water/Colorless | Orange | Colorless | Colorless |

As the data in Table 1 show, all dyes tested are a different color in PAA solution than in the two control solutions, i.e., acidic hydrogen peroxide solution and acidic water solution. Thus, any of the dyes in Table 1 could allow for the detection of PAA specifically, without interference by a similar oxidant (e.g., $H_2O_2$) or an acid (e.g., acetic acid, hydrochloric acid).

Example 2

A solution of DSSA ($4.37 \times 10^{-3}$ M) was prepared in deionized water. To RAPICIDE PA working solution (3 mL) in a quartz cuvette (3.5 mL), DSSA solution (30 μL) was added and mixed. The cuvette was immediately placed in an Agilent 8453 UV-Vis spectrometer (Agilent Technologies, Santa Clara, Calif., USA) and the absorbance at 450 nm was measured. The same procedure was carried out using an ABTS dye solution ($6.03 \times 10^{-3}$M solution in deionized water). Table 2 shows the absorbance changes over time at 450 nm for each dye solution.

TABLE 2

Change of Absorbance Values at 450 nm for DSSA and ABTS in RAPICIDE PA Solution over Time

| | Time (minutes) | | | | | | | | | | |
|---|---|---|---|---|---|---|---|---|---|---|---|
| | 1 | 2 | 3 | 4 | 5 | 6 | 7 | 8 | 10 | 15 | 20 |
| DSSA | 0.02 | 0.05 | 0.10 | 0.16 | 0.22 | 0.28 | x | 0.39 | 0.47 | 0.57 | 0.56 |
| ABTS | 0.01 | 0.02 | 0.03 | 0.04 | 0.05 | 0.06 | 0.07 | x | 0.09 | x | x | x = no measurement recorded

The data in Table 2 suggest that the reactions between PAA and DSSA or ABTS are time dependent rather than instant or rapid, which may allow for the detection of reaction time for an integrator chemical indicator.

Example 3

DSSA aqueous solutions at different concentrations were prepared by suspending DSSA in water at the weight percentages ("wt %") shown in Table 3. Aqueous ammonia (20 wt %) was added dropwise until the DSSA suspensions completely dissolved to give clear solutions. Strips approximately 3 cm by 0.5 cm of Magma nylon membrane were dipped in the solutions for about 15 seconds to coat about 1.5 cm of the length of each strip. The coated strips were removed from solution and were air-dried at room temperature (about 23° C.) overnight or at 50-80° C. for about one hour. The coated strips were then washed in a diluted INTERCEPT detergent solution (0.5% w/w) for 3 minutes and were subsequently rinsed with water and allowed to dry at room temperature.

Each coated strip was then immersed in either a 2 wt % peracetic acid ("PAA") solution or a 2 wt % $H_2O_2$ solution. Color changes of the coated strips were visually observed and are shown in Table 3. The PAA solutions contacted with coated strips prepared with less than 1.0 wt % aqueous DSSA typically remained colorless after exposure for up to five minutes to the coated strips, suggesting that in most cases, there was no DSSA leaching into the solutions.

Additional coated strips were prepared using 0.2% wt % DSSA. The strips were exposed to a 2 wt % PAA for 1-5 minutes. Exposed strips were read with an X-Rite 500 Series Spectrodensitometer (X-Rite, Incorporated, Grand Rapids, Mich.); the results are provided in Table 4.

TABLE 4

Color Change Measurement over Time with Spectrodensitometer of Nylon Membranes Coated with DSSA Exposed to 2 wt % Peracetic Acid

| Substrate | Solution | Time (min) | L* | a* | b* | $\Delta E^*_{ab}$ |
|---|---|---|---|---|---|---|
| Magma Nylon | 0.2% DSSA | 1 | 90.71 | 15.52 | 4.38 | |
| Magma Nylon | 0.2% DSSA | 2 | 86.51 | 8.82 | 18.81 | 16.46 |
| Magma Nylon | 0.2% DSSA | 3 | 90.53 | 5.17 | 12.40 | 13.10 |
| Magma Nylon | 0.2% DSSA | 4 | 81.91 | 13.10 | 24.37 | 21.98 |
| Magma Nylon | 0.2% DSSA | 5 | 76.87 | 17.91 | 29.30 | 28.61 |
| Nylon NM87701080ZN | 0.2% DSSA | 1 | 92.38 | −7.13 | −6.79 | |
| Nylon NM87701080ZN | 0.2% DSSA | 2 | 87.31 | 0.77 | −0.17 | 11.48 |
| Nylon NM87701080ZN | 0.2% DSSA | 3 | 83.30 | 10.87 | 11.71 | 27.36 |
| Nylon NM87701080ZN | 0.2% DSSA | 4 | 80.32 | 12.80 | 13.62 | 30.96 |
| Nylon NM87701080ZN | 0.2% DSSA | 5 | 82.48 | 10.93 | 12.00 | 27.87 |

As the data in Table 4 show, L*, a*, b, and $\Delta E^*_{ab}$ values change according to peracetic acid exposure time and could thus be used to monitor the progress of a decontamination process.

Example 4

DSSA dye (0.1 g) was suspended in water (50 g) and 3-aminopropyltrimethoxysilane ("APS" 0.4 g) was added

TABLE 3

Color Change of Nylon Membranes Coated with DSSA and Exposed to 2 wt % $H_2O_2$ or 2 wt % Peracetic Acid

| DSSA (aqueous) | Substrate | 2 wt % $H_2O_2$ (5 minutes) | 2 wt % Peracetic Acid (2 minutes) | 2 wt % Peracetic acid (5 minutes) | DSSA Leaching |
|---|---|---|---|---|---|
| 1.0 wt % | Nylon membrane NM87701080ZN | No change | Pale purple | Purple | Yes |
| 0.2 wt % | Nylon membrane NM87701080ZN | No change | Pale purple | Purple | No |
| 0.13 wt % | Nylon membrane NM87701080ZN | No change | Pale purple | Purple | No |
| 0.1 wt % | Nylon membrane NM87701080ZN | No change | Pale purple | Purple | No |
| 0.2 wt % | Magma Nylon membrane | No change | Pale orange | Orange-brown | No |
| 0.13 wt % | Magma Nylon membrane | No change | Pale orange | Orange-brown | No |
| 0.1 wt % | Magma Nylon membrane | No change | Pale orange | Orange-brown | No | dropwise until the DSSA was completely dissolved to give a clear solution. A strip of nylon membrane or of Magma nylon membrane was dipped in the solution to coat about 1.5 cm. The nylon strip was removes from the solution and air dried at either room temperature overnight or at 50-80° C. for about one hour. The coated strip was then washed in a detergent solution for 3 minutes (diluted INTERCEPT detergent solution, 0.33% w/w), rinsed in water and allowed to dry at room temperature. The coated strip was then immersed in a 2 wt % PAA solution, causing the appearance of the coated strip to change from colorless to deep pink over a period of 5 minutes. The PAA solution remained colorless, thus no DSSA leaching to the solution was observed.

The previous experiment was repeated, except 30% ammonium hydroxide was added dropwise in place of the APS. The solution obtained was again clear. When the coated strip was immersed in a PAA solution, a dark pink color developed over a period of 5 minutes. There is no apparent difference between using either APS or ammonia to solubilize the dye in solution.

More coated strips were prepared as described above using both the APS and ammonia solutions of DSSA. After washing and drying, the strips were immersed in a 2% solution of hydrogen peroxide. No color change occurred after 5 minutes, and no color development was observed after immersion in the hydrogen peroxide solution for 24 hours. These results indicate that color development occurs with the PAA solution but not with a hydrogen peroxide solution.

DSSA solutions (0.2 wt %) prepared with either ammonia or with APS as described above were used to coat strips of nylon membrane or of Magma nylon membrane approximately 3 cm by 0.5 cm, which were then washed with detergent solution, with water, and then dried, as described above. The strips were immersed in 2 wt % PAA solution for times of 1, 2, 3, 4, and 5 minutes. On removal from the solution the PAA-exposed strips were washed in water and dried.

Figure 2:
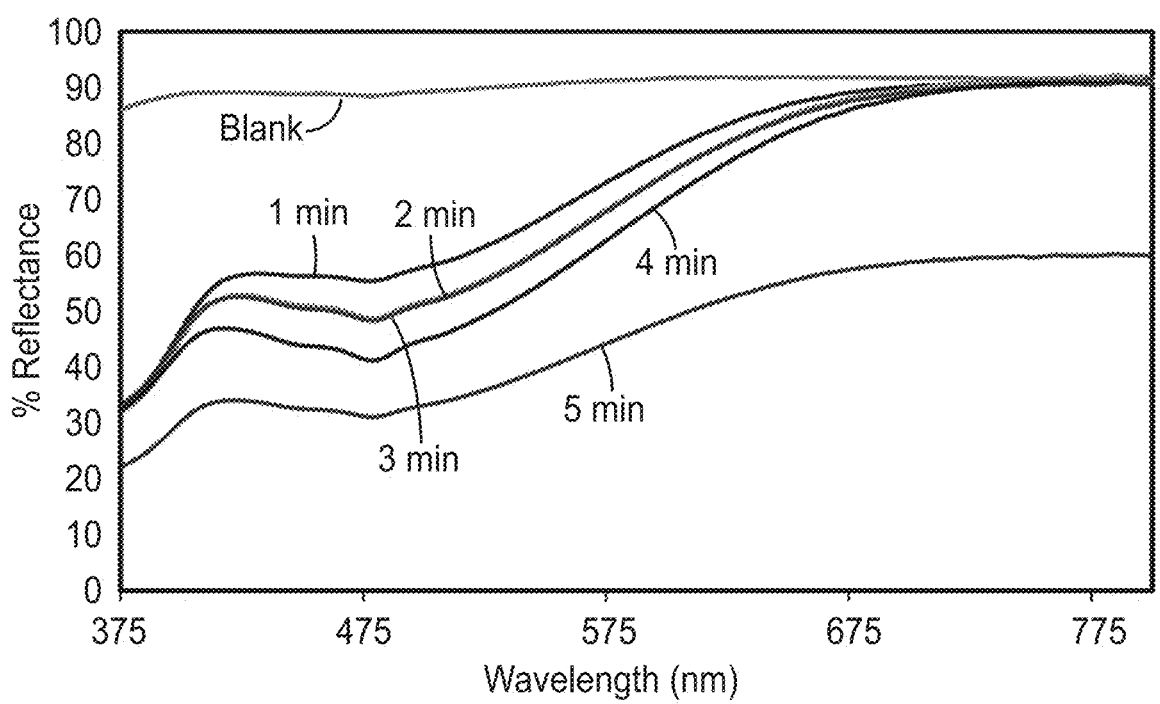
FIG. 2 is a graph of % reflectance as a function of wavelength for DSSA coated nylon membranes exposed to 2 wt % PAA solution for 1 to 5 minutes.
Figure 3:
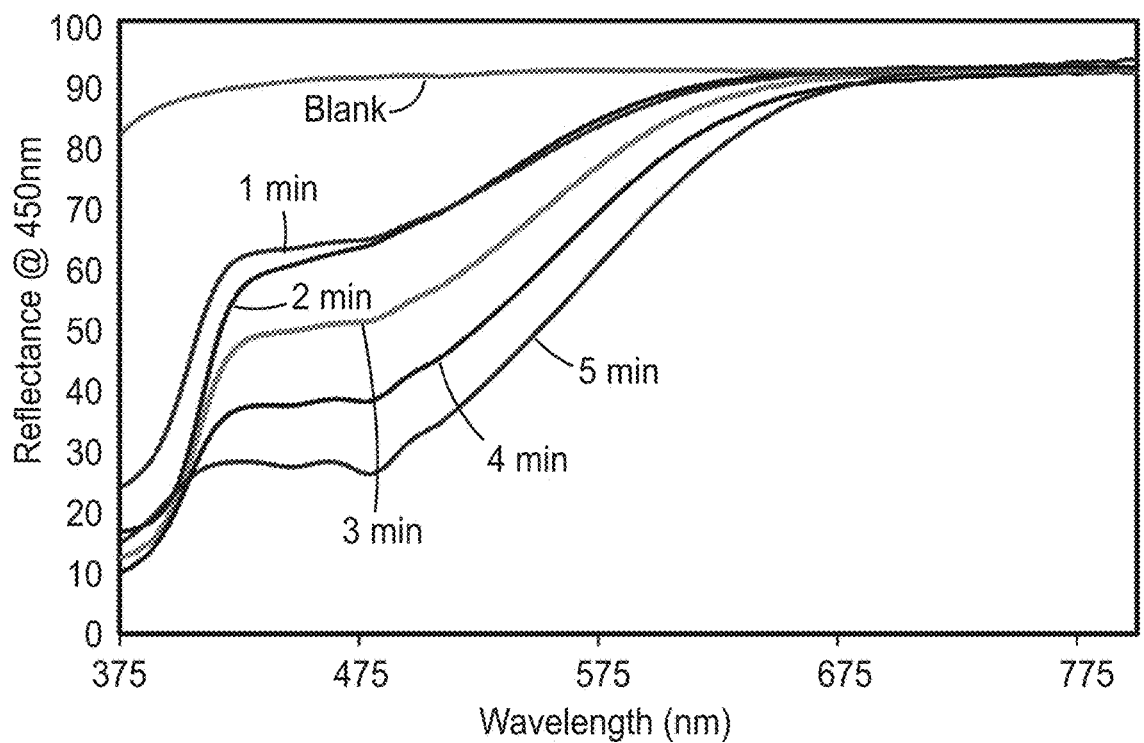
FIG. 3 is a graph of % reflectance as a function of wavelength for DSSA coated Magma nylon membranes exposed to 2 wt % PAA solution for 1 to 5 minutes.

Referring to FIGS. 2 and 3, reflectivity readings for the PAA-exposed strips were measured over 375-800 nm using a X-Rite 500 Series Spectrodensitometer (X-Rite, Incorporated, Grand Rapids, Mich.). The PAA-exposed strips show the development of color with time, indicating that DSSA-coated nylon membranes can effectively measure the progress of the reaction of DSSA in the presence of PAA in solution within 5 minutes and with a significant % reflectance separation between each minute of reaction time particularly between about 400 nm and 600 nm (e.g., 450 nm).

Example 5

DSSA (0.1 g) was suspended in water (50 g). Various amounts of 3-aminopropyltrimethoxysilane ("APS") were added to samples of the 0.2 wt % DSSA solution as provided in Table 5. For the ammonia sample, 20 wt % ammonia was added dropwise to a DSSA suspension until the DSSA dissolved, as in Example 3. Nylon membrane strips approximately 3 cm by 0.5 cm were dipped in the solutions separately to coat about 1.5 cm of the nylon membrane. Each coated nylon membrane strip was removed from solution and air dried at room temperature or at 50-80° C. Each coated nylon strip was then washed in a detergent solution (diluted INTERCEPT detergent solution, 0.33% w/w) for 3 minutes, rinsed in water, and allowed to dry at room temperature.

Each coated nylon strip was then immersed in a 2 wt % peracetic acid ("PAA") solution, where a change from colorless to deep pink occurred over a period of 5 minutes. The PAA solution remained colorless, thus no DSSA leached from the test strips into the solution. The initial time and final time for color change of the solutions were monitored and the collected data are shown in Table 5.

TABLE 5

Effect of Base Identity and Base Concentration on Color Change Developing

| Time DSSA | Substrate | Base | Initial Coating Color | Time to Develop Initial Color | Time to Develop Final Color |
|---|---|---|---|---|---|
| 0.2 wt % | Nylon membrane | NH$_3$ | Colorless | 45 s, pink | 240 s, dark pink |
| | | 0.2 wt % APS | Colorless | 70 s, pink | 300 s, dark pink |
| | | 0.6 wt % APS | Colorless | 90 s, pink | 300 s, dark pink |
| | | 1.0 wt % APS | Colorless | 120 s, pink | 360 s, dark pink |
| | | 1.4 wt % APS | Colorless | 180 s, pink | 480 s, dark pink |

As the data in Table 5 demonstrate, the time for a DSSA-coated nylon strip to develop a visible color change, i.e., a pink color, when exposed to 2 wt % PAA is dependent not only on the identity of the base used to solubilize the DSSA, e.g., aqueous ammonia, APS, but also on the concentration of the base. The presence of APS is shown to result in slower color development than when aqueous ammonia is the solubilizing base, and higher concentrations of APS result in longer color development times than lower concentrations of APS.

Example 6

A coating solution containing 0.2 wt % of DSSA and 0.8 wt % of APS was prepared in water. The solution was used to coat a nylon membrane (NM87701080ZN, "S1") and a quaternary amine-modified nylon membrane (NM87701080AM, "S1+") using gravure coating method. The coated nylon membranes were cut into 0.5 cm×10 cm strips and processed by the following steps: 1) washed with INTERCEPT detergent (0.3 wt %) for ten minutes at room temperature; 2) washed with 30° C. or 25° C. deionized water for 5 minutes; 3) exposed to RAPICIDE PA working solution (full strength (1,000 ppm PAA) or half strength (500 ppm PAA) based on the manufacturer's instructions) for 3 or 5 minutes; 4) washed with deionized water again for 10 minutes; 5) washed in ethanol for 1 minute; and 6) air dried for 20 minutes before taking a percent reflectance reading at 450 nm of the exposed strips using an X-Rite 500 Series Spectrodensitometer (X-Rite, Incorporated, Grand Rapids, Mich.). The data are provided in Table 6.

TABLE 6

Time, Temperature, and PAA Concentration Response
of DSSA Indicator % Reflectance at 450 nm

| Test Condition | 3 minutes Full Strength PAA 30° C. | 5 minutes Full Strength PAA 30° C. | 5 minutes Full Strength PAA 25° C. | 5 minutes Half Strength PAA 30° C. |
|---|---|---|---|---|
| S+ | 27.53 ± 044 | 16.88 ± 0.33 | 22.77 ± 0.26 | 32.43 ± 0.47 |
| S  | 62.12 ± 1.31 | 49.89 ± 1.20 | 55.83 ± 1.16 | 64.45 ± 1.11 |

As the data in Table 6 show, the constructed chemical indicator may be used to distinguish between exposure to a decontamination cycle that would provide adequate decontamination, e.g., 30° C. for 5 min and 1000 ppm of PAA, versus other conditions that would not provide adequate decontamination, such as, for example, a 3-minute exposure time, half of the recommended PAA concentration, or a 25° C. processing temperature, by evaluating the change in reflectance at 450 nm of the chemical indicator.

Test Method for Examples 7-14

Coated test specimens were cut into 0.5 cm×6 cm strips. Test specimens were exposed to three testing solutions to simulate the endoscope washing cycles. The temperature of the solutions was controlled using a circulating water bath at 30° C. connected to three testing vessels, which contained the testing solutions. The exposure time and conditions are as follows: 10 minutes exposure of the test strips in 0.33% INTERCEPT Detergent, 5 minutes in water at 30° C., and 3 or 5 minutes (as indicated in the Tables associated with Examples 7-14) in RAPICIDE PA solutions of various dilutions at 30° C., followed by 10 minutes in water for rinse. Lastly, the strips were rinsed in 70% isopropanol solution for 30 seconds. The strips were dried with a paper towel and their reflectance at 450 nm was measured using an X-Rite 500 Series Spectrodensitometer (X-Rite, Incorporated, Grand Rapids, Mich.). Haze, i.e., cloudiness of the colored coating, and leaching of the DSSA into the PAA solution were evaluated visually, i.e., qualitatively.

Example 7

Coating solutions were prepared using formulations shown in Table 7 by placing DSSA, deionized water, and concentrated ammonia solution (30 wt %) in a flask. Percentages in Table 7 refer to the final wt % of each formulation, the remaining balance being water. The solution was stirred to completely dissolve the solid DSSA. To the coating solution was added 3-(2-aminoethyl)aminopropyl trimethoxysilane ("AEAPS") as indicated in the Table 7. To the coating solution was then added one or more polymer latexes to obtain coating solutions containing 20 wt % polymer, as indicated in Table 7. The coating solutions containing mixtures of polymer latexes were obtained by mixing individual polymer latex solutions prepared as described above in the desired ratio as provided in Table 7. To each of these coating solutions was added a PolyAziridine crosslinker (PZ-28). Each resulting solution was coated on a clear PET film substrate with a Mayer bar #24, and were subsequently dried and cured at 120° C. for 5 minutes. The final coated and cured PET film was tested and evaluated as described above in Test Method for Examples 7-14. The results of the testing are provided in Table 8.

TABLE 7

Indicator Composition Formulations

| Sample Number | DSSA | Ammonia (30% Aqueous) | AEAPS | Polymer Latex Weight Ratio (20 wt % Total) | | | | PZ-28 | Nalco 2326 |
| | | | | R966 | A1049 | UD420 | A612 | | |
|---|---|---|---|---|---|---|---|---|---|
| 1  | 1% | 3% | 0.50% | 100% | —    | —    | —    | 1% | —  |
| 2  | 1% | 3% | 0.50% | 100% | —    | —    | —    | 1% | 5% |
| 3  | 1% | 3% | 0.50% | —    | 100% | —    | —    | 1% | —  |
| 4  | 1% | 3% | 0.50% | 70%  | 30%  | —    | —    | 1% | —  |
| 5  | 1% | 3% | 0.50% | 50%  | 50%  | —    | —    | 1% | —  |
| 6  | 1% | 3% | 0.50% | 30%  | 70%  | —    | —    | 1% | —  |
| 7  | 1% | 3% | 0.50% | —    | —    | 100% | —    | 1% | —  |
| 8  | 1% | 3% | 0.50% | 70%  | —    | 30%  | —    | 1% | —  |
| 9  | 1% | 3% | 0.50% | 50%  | —    | 50%  | —    | 1% | —  |
| 10 | 1% | 3% | 0.50% | 30%  | —    | 70%  | —    | 1% | —  |
| 11 | 1% | 3% | 0.50% | —    | —    | —    | 100% | 1% | —  |
| 12 | 1% | 3% | 0.50% | 70%  | —    | —    | 30%  | 1% | —  |
| 13 | 1% | 3% | 0.50% | 50%  | —    | —    | 50%  | 1% | —  |
| 14 | 1% | 3% | 0.50% | 30%  | —    | —    | 70%  | 1% | —  |

TABLE 8

Percent Reflectance, Haze, and Leaching Results

| | Percent Reflectance ("% R") at 450 nm | | | | |
| Sample Number | Measured at 3 minutes | Measured at 5 minutes | Delta % R (3 minutes minus 5 minutes) | Haze | Leaching |
|---|---|---|---|---|---|
| 1  | 42.4  | 16.8   | 25.6  | Yes | No |
| 2  | 76.54 | 76.26  | 0.28  | Yes | No |
| 3  | 60.56 | 54.315 | 6.245 | No  | No |
| 4  | 62.13 | 55.435 | 6.695 | Yes | No |
| 5  | 64.29 | 56.572 | 7.718 | Yes | No |
| 6  | 62.76 | 55.87  | 6.89  | Yes | No |
| 7  | 47.38 | 30.32  | 17.06 | No  | No |
| 8  | 58.36 | 42.5   | 15.86 | No  | No |
| 9  | 54.11 | 38.02  | 16.09 | No  | No |
| 10 | 52.19 | 34.51  | 17.68 | No  | No |
| 11 | 67.21 | 62.91  | 4.3   | No  | No |

TABLE 8-continued

Percent Reflectance, Haze, and Leaching Results

Percent Reflectance ("% R") at 450 nm

| Sample Number | Measured at 3 minutes | Measured at 5 minutes | Delta % R (3 minutes minus 5 minutes) | Haze | Leaching |
|---|---|---|---|---|---|
| 12 | 43.5 | 28.94 | 14.56 | Yes | No |
| 13 | 50.46 | 34.98 | 15.48 | Yes | No |
| 14 | 51.91 | 32.71 | 19.2 | Yes | No |

The data in Table 8 show that chemical indicators with desirable hazing and leaching characteristics, i.e., no hazing and no leaching, and a measurable Delta % R from 3-5 minutes may be prepared using AEAPS and ammonia as solubilizing bases and various polymer latexes that allow the chemical indicator composition to be coated on a PET film at a DSSA concentration of 1 wt %.

Example 8

Coating solutions were prepared according to the formulations in Table 9 by placing into a flask DSSA, deionized water, and concentrated ammonia (30 wt %). The solutions were stirred to completely dissolve the solid DSSA. To each solution was added 3-(2-aminoethyl)aminopropyl trimethoxy-silane ("AEAPS"). To each solution was then added the polyurethane latex NEOREZ R966. To each solution was then added a PolyAziridine crosslinker (PZ-28). Percentages in Table 9 refer to the final wt % of each formulation, the remaining balance being water. The resulting solution was coated on a clear PET substrate with a Mayer bar #24, and were subsequently dried and cured at 120° C. for 5 minutes. The final coated and cured PET films were tested and evaluated as described above in Test Method for Examples 7-14. The results of the testing are provided in Table 9.

The data in Table 9 show that chemical indicators with desirable hazing and leaching characteristics, i.e., no hazing and no leaching, and a measurable Delta % R from 3-5 minutes may be prepared using AEAPS and ammonia as solubilizing bases and an aliphatic urethane polymer latex that allow the chemical indicator composition to be coated on a PET film at a DSSA concentration of 0.80-1.20 wt %. The results further suggest that desirable hazing characteristics particularly may be achieved with an increase in crosslinker in the indicator composition formulation from 1 wt % to 2 wt %.

Example 9

Coating solutions as described in Table 10 were prepared for coating trials. Percentages in Table 10 refer to the final wt % of reagents in each formulation. Into a large flask was placed DSSA, deionized water, and concentrated ammonia (30 wt %). The solution was stirred to completely dissolve the solid DSSA. To the solution was added 3-(2-aminoethyl) aminopropyl trimethoxy-silane (AEAPS) as indicated in the Table 10. To the coating solution was added a polymer latex to obtain 20 wt % of polymer solids in the coating solution. The coating solutions containing mixtures of polymer latexes were obtained by mixing the two individual solutions prepared as described above in desired ratios as provided in Table 10. To the solution was then added a PolyAziridine crosslinker (PZ-28). Percentages in Table 10 refer to the final wt % of each formulation, the remaining balance being water. The resulting solution was coated on a clear PET substrate (5 mil thick, Rhoplex-primed) on a pilot coating line with a slot-die coater using the pump speeds provided in Table 10 for coating weight control. The coated substrates were subsequently dried and cured at 130° C. for 2 minutes. Each sample of the cured, coated PET film was tested and evaluated using the previously described Test Method for Examples 7-14. The results of the testing are provided in Table 10.

TABLE 9

Indicator Composition Formulations and Percent Reflectance, Haze, and Leaching Results

| | | | | | Percent Reflectance (% R) at 450 nm | | | | |
|---|---|---|---|---|---|---|---|---|---|
| Sample Number | DSSA | Ammonia (30% Aqueous) | AEAPS | R966 Polymer Latex Final wt % | PZ-28 | Measured at 3 minutes | Measured at 5 minutes | Delta % R (3 minutes minus 5 minutes) | Haze | Leaching |
| 1 | 1% | 3% | 0.50% | 20% | 2% | 56.47 | 41.57 | 14.9 | No | No |
| 2 | 1% | 3% | 2% | 20% | 1% | 55.7 | 34.48 | 21.22 | Yes | No |
| 3 | 1% | 3% | 2% | 20% | 1% | 56 | 35.67 | 20.33 | Yes | No |
| 4 | 1% | 3% | 1.50% | 20% | 1% | 53.26 | 34.15 | 19.11 | Yes | No |
| 5 | 1% | 3% | 1.00% | 20% | 1% | 49.37 | 32.06 | 17.31 | Yes | No |
| 6 | 1% | 3% | 0.50% | 20% | 1% | 47.91 | 24.08 | 23.83 | Yes | No |
| 7 | 1.50% | 4.50% | 3% | 20% | 1% | 35.94 | 21.31 | 14.63 | Yes | No |
| 8 | 2% | 6% | 4% | 20% | 1% | 29.44 | 18.18 | 11.26 | Yes | No |
| 9 | 1% | 1% | 0.50% | 20% | 2% | 62.04 | 45.71 | 16.33 | No | No |
| 10 | 1% | 2% | 0.50% | 20% | 2% | 61.72 | 44.3 | 17.42 | No | No |
| 11 | 1% | 3% | 0.50% | 20% | 2% | 59.33 | 42.22 | 17.11 | No | No |
| 12 | 0.80% | 2.40% | 0.50% | 20% | 2% | 61.535 | 47.765 | 13.77 | No | No |
| 13 | 1.20% | 3.60% | 0.50% | 20% | 2% | 60.525 | 38.465 | 22.06 | No | No |

TABLE 10

Indicator Composition Formulations and Percent Reflectance, Haze, and Leaching Results

| Sample Number | DSSA | Ammonia (30% Aqueous) | AEAPS | Polymer Latex Weight Ratio (20 wt % Total) | | | Percent Reflectance (% R) at 450 nm | | Delta % R (3 minutes minus 5 minutes) | Haze | Leaching | Pump Speed (cc/min) |
|---|---|---|---|---|---|---|---|---|---|---|---|---|
| | | | | UD420 | R966 | PZ-28 | Measured at 3 minutes | Measured at 5 minutes | | | | |
| 1 | 1% | 3% | 0.50% | 100% | — | 2% | 67.61 | 50.24 | 17.37 | No | No | 5 |
| 2 | 1% | 3% | 0.50% | 100% | — | 2% | 68.62 | 54.86 | 13.76 | No | No | 7.5 |
| 3 | 1% | 3% | 0.50% | 100% | — | 2% | 69.92 | 54.27 | 15.65 | No | No | 10 |
| 4 | 1% | 3% | 0.50% | 30% | 70% | 2% | 61.81 | 46.91 | 14.9 | No | No | 5 |
| 5 | 1% | 3% | 0.50% | 30% | 70% | 2% | 62.8 | 46.29 | 16.51 | No | No | 7.5 |
| 6 | 1% | 3% | 0.50% | 30% | 70% | 2% | 61.51 | 45.51 | 16 | No | No | 10 |
| 7 | 1% | 3% | 0.50% | — | 100% | 2% | 57.62 | 36.51 | 21.11 | No | No | 5 |
| 8 | 1% | 3% | 0.50% | — | 100% | 2% | 57.71 | 39.24 | 18.47 | No | No | 7.5 |
| 9 | 1% | 3% | 0.50% | — | 100% | 2% | 57.41 | 34.75 | 22.66 | No | No | 10 |

The data in Table 10 show that various polyurethane resins can be used in chemical indicators of the present disclosure. The difference in "pass" conditions (e.g., 5 min exposure) and "fail" conditions (e.g., 3 min exposure) is relatively similar over the range of coat weights resulting from varying pump speeds.

Example 10

Coating solution preparation for Table 11 below: Into a flask was placed DSSA, deionized water, and concentrated ammonia (30 wt %). The solution was stirred to completely dissolve the solid DSSA. To the solution was added 3-(2-aminoethyl)aminopropyl trimethoxysilane (AEAPS). To the solution was added polyurethane R966 or polyacrylic A612 latex to obtain a mixed solution. To the stable solution was added a PolyAziridine crosslinker (PZ-28, see Table 11 for amounts). Percentages in Table 11 refer to the final wt % of each formulation, the remaining balance being water. The resulting solution was coated on a clear PET substrate with a Mayer bar #24, and subsequently dried and cured at 120° C. for 5 minutes. The final coated and cured film was evaluated using the previously described test method for Test Method for Examples 7-14. The results of the testing are provided in Table 11.

As the data in Table 11 show, the change in percent reflectance may be altered by changing the coating resin or the crosslinker concentration, as demonstrated by the varying percent reflectance values at three and/or five minutes.

Example 11

Coating solution preparation for Table 12 below: Into a flask was placed DSSA, deionized water, and concentrated ammonia (30 wt %). To the solution was a mixture of polyurethane R966 latex and Nalco 2327 colloidal silica in ratios as described in Table 12 to obtain 20 wt % total latex and silica in the coating solution. To the stable solution was added a PolyAziridine crosslinker (PZ-28). Percentages in Table 12 refer to the final wt % of each formulation, the remaining balance being water. The resulting coating solution was coated on a clear PET substrate with a Mayer bar #24, and subsequently dried and cured at 120° C. for 5 minutes. The final coated and cured films were evaluated according to the previously described Test Method for Examples 7-14. The results are provided in Table 12.

TABLE 11

Indicator Composition Formulations and Percent Reflectance, Haze, and Leaching Results

| Sample Number | DSSA | Ammonia (30 wt %) | AEAPS | Polymer Latex (wt % Polymer) | PZ-28 | Percent Reflectance (% R) at 450 nm | | Delta % R (3 minutes minus 5 minutes) | Haze | Leaching |
|---|---|---|---|---|---|---|---|---|---|---|
| | | | | | | Measured at 3 minutes | Measured at 5 minutes | | | |
| 1 | 1% | 1% | 0.50% | A612 (10) | 2% | 69.39 | 64.52 | 4.87 | No | No |
| 2 | 1% | 1% | 0.00% | R966 (20) | 2% | 58.33 | 35.26 | 23.07 | No | No |
| 3 | 1% | 1% | 0.50% | R966 (20) | 2% | 54.72 | 33.29 | 21.43 | No | No |
| 4 | 1% | 1% | 0.50% | R966 (20) | 1.5% | 53.12 | 31.06 | 22.06 | No | No |
| 5 | 1% | 1% | 0.50% | R966 (20) | 1% | 54.43 | 29.1 | 25.33 | No | No |

TABLE 12

Indicator Composition Formulations and Percent Reflectance, Haze, and Leaching Results

| | | | | | | Percent Reflectance (% R) at 450 nm | | | | |
| --- | --- | --- | --- | --- | --- | --- | --- | --- | --- | --- |
| Sample Number | DSSA | Ammonia (30 wt %) | R966 | 2327 | PZ-28 | Measured at 3 minutes | Measured at 5 minutes | Delta % R (3 minutes minus 5 minutes) | Haze | Leaching |
| 1 | 1% | 1% | 20% | 0% | 1% | 52.40 | 32.32 | 20.08 | No | No |
| 2 | 1% | 1% | 18% | 2% | 1% | 52.20 | 33.06 | 19.14 | No | No |
| 3 | 1% | 1% | 16% | 4% | 1% | 56.87 | 46.28 | 10.59 | No | No |
| 4 | 1% | 1% | 14% | 6% | 1% | 66.16 | 62.06 | 4.10 | No | No |

As the data in Table 12 show, the change in percent reflectance may be altered by changing the resin concentration in the final formulation, as demonstrated by the varying percent reflectance values.

As the data in Table 13 show, the change in percent reflectance decreased with addition of Nalco 2326 colloidal silica to the chemical indicator composition formulation.

Example 12

Coating solution preparation for Table 13 below: Into a flask was placed DSSA, deionized water, and concentrated ammonia (30 wt %). To the solution was added a mixture of polyurethane R966 latex and Nalco 2327 colloidal silica (aqueous solution) in ratios as described in Table 13 to obtain 20 wt % total latex and silica in the coating solution. To the stable solution was added a PolyAziridine crosslinker (PZ-28). Percentages in Table 13 refer to the final wt % of each formulation, the remaining balance being water. The resulting solution was coated on a clear PET substrate with a Mayer bar #24, and subsequently dried and cured at 120° C. for 5 minutes. The final coated film was tested and evaluated in the described Test Method for Examples 7-14. The results are provided in Table 13.

Example 13

Coating solution preparation for Table 14 below: Into a flask was placed DSSA, deionized water, and concentrated ammonia (30 wt %). To the solution was added a mixture of polyurethane UD-420 latex and Nalco 2327 colloidal silica in ratios as described in Table 14 to obtain a combined total of 20 wt % solutions. To the stable solution was added a PolyAziridine crosslinker (PZ-28). Percentages in Table 14 refer to the final wt % of each formulation, the remaining balance being water. The resulting solution was coated on a clear PET substrate with a Mayer bar #24, and subsequently dried and cured at 120° C. for 5 minutes. The final coated film was tested and evaluated in the described Test Method for Examples 7-14. The results are provided in Table 14.

TABLE 13

Indicator Composition Formulations and Percent Reflectance, Haze, and Leaching Results

| | | | | | | Percent Reflectance (% R) at 450 nm | | | | |
| --- | --- | --- | --- | --- | --- | --- | --- | --- | --- | --- |
| Sample Number | DSSA | Ammonia (20 wt %) | R966 | 2326 | PZ-28 | Measured at 3 minutes | Measured at 5 minutes | Delta % R (3 minutes minus 5 minutes) | Haze | Leaching |
| 1 | 1% | 1% | 20% | 0% | 1% | 52.40 | 32.32 | 20.08 | No | No |
| 2 | 1% | 1% | 18% | 2% | 1% | 54.54 | 39.68 | 14.86 | No | No |
| 3 | 1% | 1% | 16% | 4% | 1% | 61.52 | 54.18 | 7.34 | No | No |
| 4 | 1% | 1% | 14% | 6% | 1% | 67.31 | 65.29 | 2.02 | No | No |

TABLE 14

Indicator Composition Formulations and Percent Reflectance, Haze, and Leaching Results

| | | | | | Percent Reflectance (% R) at 450 nm | | | | |
|---|---|---|---|---|---|---|---|---|---|
| Sample Number | DSSA | Ammonia (30 wt %) | UD-420 | 2327 | PZ-28 | Measured at 3 minutes | Measured at 5 minutes | Delta % R (3 minutes minus 5 minutes) | Haze | Leaching |
| 1 | 1% | 1% | 20% | 0% | 1% | 54.60 | 46.15 | 8.45 | No | Yes |
| 2 | 1% | 1% | 18% | 2% | 1% | 51.36 | 40.84 | 10.52 | No | No |
| 3 | 1% | 1% | 16% | 4% | 1% | 54.66 | 39.59 | 15.07 | No | No |
| 4 | 1% | 1% | 14% | 6% | 1% | 54.96 | 46.73 | 8.23 | No | No |

As the data in Table 14 show, the change in percent reflectance increased with addition of 2 wt % and 6 wt % of Nalco 2327 colloidal silica to the chemical indicator composition. formulation.

Example 14

Coating solution preparation for Table 16 below: Into a flask was placed DSSA, deionized water, AEAPS, and concentrated ammonia (30 wt %). To the solution was added a polyurethane latex as described in Table 15 to obtain 20 wt % solutions. To the stable solution was added a PolyAziridine crosslinker (PZ-28). Percentages in Table 15 refer to the final wt % of each formulation, the remaining balance being water. The resulting solution was coated on a clear PET substrate with a Mayer bar #24, and subsequently dried and cured at 120° C. for 5 minutes. The final coated film was tested and evaluated in the described Test Method for Examples 7-14. The results are summarized in Table 15.

as shown in Table 17. Then the amount of ammonia solution indicated in Table 16 was added with stirring at room temperature until the DSSA was completely dissolved. To the solution AEAPS and latex R966 were added and mixed overnight. To the mixture was added 1 gram of PolyAziridine crosslinker PZ-28 and the solution was mixed well. The resulting clear solution was coated on PET substrate with a #26 Mayer bar and dried at 130° C. for 2 minutes. The resulting coated and cured film samples were cut into 0.5 cm×6 cm strips. The strips were placed in 850 ppm PAA solution, prepared according to the manufacturer's instructions, for 1, 2, 3, or 4 minutes. For one set of strips, the PAA solution was stirred. For a second set of strips, the PAA solution was not agitated. For the stirring experiment, the solution was agitated with a magnetic stirring bar at 300 rpm on a stirring plate. The % R of each film sample was measured at 450 nm using an X-Rite 500 Series Spectrodensitometer (X-Rite, Incorporated, Grand Rapids, Mich.).

TABLE 15

Indicator Composition Formulations and Percent Reflectance, Haze, and Leaching Results

| | | | | | | Percent Reflectance (% R) at 450 nm | | | | |
|---|---|---|---|---|---|---|---|---|---|---|
| Sample Number | DSSA | Ammonia (20 wt %) | AEAPS | PU (20 wt %) | | PZ-28 | Measured at 3 minutes | Measured at 5 minutes | Delta % R (3 minutes minus 5 minutes) | Haze | Leaching |
| 1 | 1% | 1% | 0.50% | R966 | | 1% | 58.19 | 35.90 | 22.29 | No | No |
| 2 | 1% | 1% | 0.50% | UD420 | | 1% | 49.92 | 34.27 | 15.65 | No | No |
| 3 | 1% | 1% | 0.50% | R600 | | 1% | 56.39 | 51.61 | 4.78 | Yes | Yes |
| 4 | 1% | 1% | 0.50% | R960 | | 1% | 38.73 | 30.59 | 8.14 | No | No |

As the results in Table 15 show, of the polyurethane resins examined, NEOREZ R966 provides for indicator compositions that result in no haze and no leaching while providing the largest difference between 450 nm percent reflectance readings at three minutes and five minutes.

Examples 7-14 suggest that the preferred coating formulation, i.e., chemical indicator composition, is one that consists of at least 20% NEOREZ R966 polyurethane resin and at least 1% PZ-28 coating resin. This combination results in no leaching or coating haze and provides the biggest difference between 450 nm reflectance readings for the given pass and fail cycles (5 and 3 min peracetic acid solution exposure times respectively).

Example 15

Formulations are summarized in Table 16. Into a 250 mL brown glass jar, 1 gram of DSSA was added and then water The difference between 3 and 5 minutes exposure to PAA solution is also provided as "Delta between 3 & 5 min".

TABLE 16

Effect of PAA Solution Stirring on % Reflectance

| | Formulations (in % w/w) | | | |
|---|---|---|---|---|
| | 1 | 2 | 3 | 4 |
| DSSA | 1 | 1 | 1 | 1 |
| 30% Ammonia | 1 | 1 | 1.5 | 2 |
| AEAPS | 0 | 0.5 | 2 | 2 |
| R966 (31% solids) | 64.5 | 64.5 | 64.5 | 64.5 |
| PZ-28 | 1 | 1 | 1 | 1 |
| Water | 32.5 | 32 | 30 | 29.5 |
| Total | 100 | 100 | 100 | 100 |

TABLE 16-continued

Effect of PAA Solution Stirring on % Reflectance

| | Formulations (in % w/w) | | | |
|---|---|---|---|---|
| | 1 | 2 | 3 | 4 |
| % Reflectance at 450 nm | | | | |
| 3 min (stir) | 33.88 | 37.54 | 53.04 | 52.65 |
| 5 min (stir) | 10.08 | 16.27 | 34.75 | 34.38 |
| Delta between 3 & 5 min | 23.80 | 21.27 | 18.29 | 18.28 |
| 5 min (no stir) | 10.56 | 21.70 | 43.95 | 43.03 |
| Delta between No stir & stir, 5 min | 0.48 | 5.44 | 9.20 | 8.65 |

As the data in Table 16 show, there is a measurable difference in % Reflectance ("Delta") between samples that were stirred and those that were not, with samples including 2% AEAPS showing the greatest % Reflectance difference between stirred samples and samples that were not stirred. These results suggest that the disclosed chemical indicators may be used to distinguish between decontamination processes with adequate solution flow and decontamination processes where solution flow is not adequate.

Example 16

A DSSA stock solution was prepared by adding 500 mg of DSSA dye to 50 mL of 0.1 N NaOH and stirring until the dye was completely dissolved. 10 g of 3-(trimethylammonium)-propyl-functionalized silica gel, carbonate, was added to the DSSA stock solution. The silica was mixed with the stock solution for approximately 2 hours. The silica was collected by vacuum filtration, washed with 200 mL of deionized water, and dried at 100° C. for approximately 10 minutes.

The dried silica with adsorbed DSSA dye (0.18 wt %) was spread onto a pressure sensitive adhesive with a clear backing ("PSA"). Light pressure was used to ensure that the silica was sufficiently adhered before gently shaking to remove excess silica particles. The adhesive was cut into strips approximately 3"×1" in size.

Figure 4:
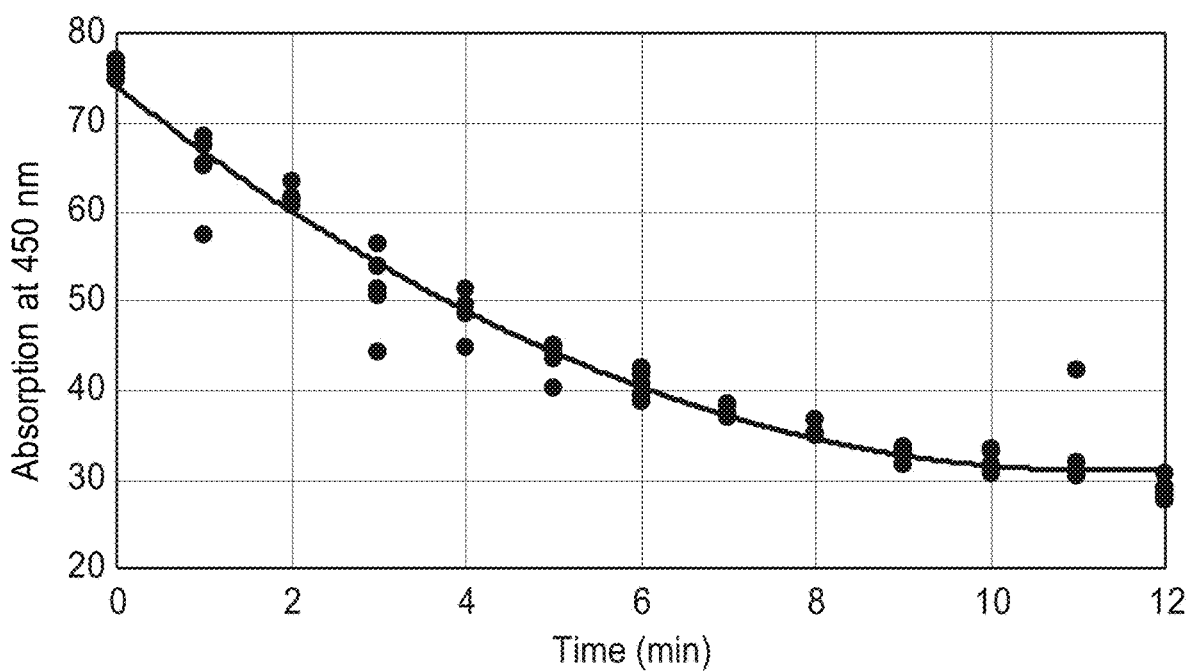
FIG. 4 is a graph of reflectance at 450 nm of adhesive strips coated with silica having 0.18 wt % adsorbed DSSA dye and reacted with a 0.1% peracetic acid solution for 0-12 minutes.

A 0.1% peracetic acid solution was prepared by diluting Medivators RAPICIDE PA to the manufacturer-recommended concentration (1:1:48, Solution A:Solution B:Water). Strips including the silica with adsorbed DSSA were added into the peracetic acid solution and removed every minute for twelve minutes to perform reflectance readings at 450 nm with an X-Rite EXACT portable spectrophotometer (X-Rite, Incorporated, Grand Rapids, Mich.) against a white background. Results are shown in FIG. 4. Referring to FIG. 4, the reflectance at 450 nm measured on the strips changed significantly over time. The described indicator composition consisting of DSSA coated onto functionalized silica powder and coated onto a clear PSA may be used to monitor high-level disinfection or sterilization processes as evidenced by the time dependence of the 450 nm reflectance readings.

Example 17

An ABTS dye stock solution was prepared by adding 71 mg of ABTS to 5 mL of water and stirring until the dye was completely dissolved. One gram of Silicycle SILIABOND chloride was added to the stock solution and mixed for approximately 10 minutes. The silica was collected by vacuum filtration, washed with 25 mL of deionized water, and dried at 100° C. for approximately 1 hour.

The dried silica with adsorbed ABTS dye (5.54 wt %) was spread onto a pressure sensitive adhesive with a clear backing. Light pressure was used to ensure that the silica was sufficiently adhered before gently shaking to remove excess silica particles. The adhesive was cut into strips approximately 3"×1" in size.

Figure 5:
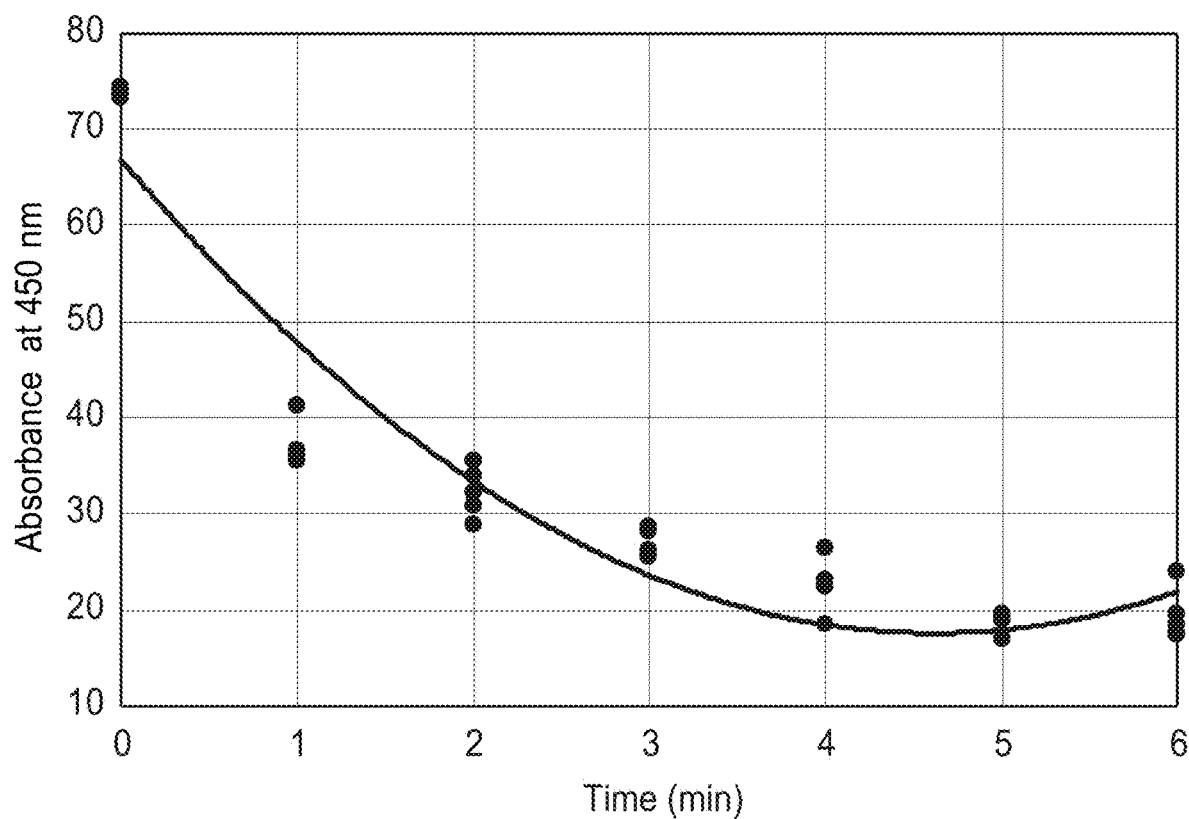
FIG. 5 is a graph of reflectance at 450 nm of adhesive strips coated with silica having 5.54 wt % adsorbed ABTS dye and reacted with a 0.1% peracetic acid solution for 0-6 minutes.

A 0.1% peracetic acid solution was prepared by diluting Medivators RAPICIDE PA to the manufacturer-recommended concentration (1:1:48, Solution A:Solution B:Water). Strips were added into the peracetic acid solution and pulled at various time intervals to perform reflectance readings with an X-Rite EXACT portable spectrophotometer (X-Rite, Incorporated, Grand Rapids, Mich.) against a white background. Results are shown in FIG. 5. Referring to FIG. 5, the reflectance at 450 nm measured on the strips changes significantly over time. The described indicator composition consisting of ABTS coated onto functionalized silica powder and coated onto a clear PSA may be used to monitor high-level disinfection or sterilization processes as evidenced by the time dependence of the 450 nm reflectance readings.

Example 18

The dye adsorbing efficiency of Sigma-Aldrich and Silicycle trimethylammonium functionalized silica with carbonate counterions and a Silicycle trimethylammonium functionalized silica with chloride counterions were compared. Stock solutions of DSSA and ABTS dyes were prepared in 0.1N NaOH and water respectively and the solutions were stirred until the dyes were dissolved. Silicas were added to DSSA and ABTS stock solutions and stirred for approximately 1 hour. The silica was collected by vacuum filtration, washed with DI water, and dried at 100° C. for approximately 10 minutes. Absorbency readings were performed on diluted samples of the filtrates to determine the mass of dye still in solution using the molar attenuation coefficients determined in example 1 for DSSA and ABTS at 340 nm.

TABLE 19

DSSA and ABTS Dyes Adsorbed onto Trimethylammonium Functionalized Silica

| Dye Vendor | Silica Vendor/Counterion | Dye | Dye Concentration (mM) | Silica/Solution Ratio | % Dye Adsorbed |
|---|---|---|---|---|---|
| TCI | Sigma/Carbonate | DSSA | 51 | 0.3 | 37 |
| TCI | Silicycle/Carbonate | DSSA | 51 | 0.3 | 20 |
| TCI | Silicycle/Chloride | DSSA | 51 | 0.3 | 98 |
| Amresco | Silicycle/Chloride | ABTS | 8.3 | 0.2 | 78 |
| Amresco | Sigma/Carbonate | ABTS | 26 | 0.2 | 100 |

Referring to Table 20, there was a significant difference in dye adsorbance depending on the silica source, with Silicycle silica containing carbonate counterions more efficiently adsorbing DSSA dye than Sigma-Aldrich silica with carbonate counterions. The best adsorbance efficiency was observed for Silicycle silica with chloride counterion, which adsorbs approximately 98% of DSSA and 100% of ABTS in solution.

Example 19

Samples of trimethylammonium functionalized silica were prepared with DSSA dye as in Example 16 using the SiliCycle SILIABOND Chloride silica gel. The silica was spread onto a clear PSA and cut into test strips. The test strips were exposed to the following cycle which was intended to mimic a cycle in a Medivators automatic endoscope reprocessing machine: 10 min in 0.33% Medivators INTERCEPT Detergent, 5 min in water (controlled temperature), 3-5 minutes in Medivators RAPICIDE PA at various dilutions (controlled temperature), 10 minutes in water, 1 minute in ethanol. The time, temperature, and concentration of the Medivators RAPICIDE PA step was varied to show that the measured percent reflectance of the test strips at the end of the cycle could detect these changes and ultimately detect deficiencies in the required exposure to sterilant. Percent reflectance readings at 450 nm were performed with an X-Rite EXACT portable spectrophotometer (X-Rite, Incorporated, Grand Rapids, Mich.) on the reacted strips against a white background. Results are shown in Tables 20 and 21.

As can be seen from the data in Tables 20 and 21, there is a significant difference between reflectance readings at 5 minutes in 25° C., 30° C., and 35° C. There is also a significant difference between reflectance readings at 3 and 5 minutes at each temperature. These results suggest that the color of the disclosed chemical indicator has a dependence on PAA exposure time, temperature, and concentration. This chemical indicator could therefore be used to detect whether a high-level disinfection or sterilization process was deficient in any one of these three parameters.

Example 20

Samples of trimethylammonium functionalized silica were prepared with ABTS dye as in example 17 using the Silicycle SILIABOND Chloride silica gel. The silica was spread onto a clear PSA and cut into test strips. The test strips were exposed to the following cycle which was intended to mimic a cycle in a Medivators automatic endoscope reprocessing machine: 10 min in 0.33% Medivators INTERCEPT Detergent, 5 min in water (controlled temperature), 3-5 minutes in Medivators RAPICIDE PA at various dilutions (controlled temperatures), 10 minutes in water, 1 minute in ethanol. The time, temperature, and concentration of the Medivators RAPICIDE PA step was varied to show that the measured reflectance of the test strips at the end of the cycle could detect these changes and ultimately detect deficiencies in the required exposure to sterilant. Percent reflectance readings at 450 nm with an X-Rite EXACT portable spectrophotometer (X-Rite, Incorporated, Grand Rapids, Mich.) on the reacted strips against a white background. Results are shown in Tables 22 and 23.

TABLE 20

Percent Reflectance at 450 nm for Chemical Indicators Including DSSA Exposed to Various Decontamination Conditions

| Conditions (Full strength PAA used in all) | 3 minutes 25° C. | 5 minutes 25° C. | 3 minutes 30° C. | 5 minutes 30° C. | 3 minutes 35° C. | 5 minutes 35° C. |
|---|---|---|---|---|---|---|
| Percent reflectance at 450 nm | 55.02 ± 1.10 | 41.70 ± 1.32 | 40.36 ± 1.31 | 34.98 ± 1.09 | 36.37 ± 1.18 | 27.92 ± 0.92 |

TABLE 21

Percent Reflectance at 450 nm for Chemical Indicators Including DSSA Exposed to Various Decontamination Conditions

| | Conditions | | | |
|---|---|---|---|---|
| | 5 minutes Full strength PAA 30° C. | 5 minutes 0.8x Strength PAA 25° C. | 5 minutes Full Strength PAA 35° C. | 5 minutes 0.8x Strength PAA 35° C. |
| Percent reflectance at 450 nm | 34.98 ± 1.10 | 46.38 ± 2.12 | 27.92 ± 0.92 | 38.97 ± 1.47 |

TABLE 22

Percent Reflectance at 450 nm for Chemical Indicators Including
ABTS Exposed to Various Decontamination Conditions

| Conditions (full strength PAA used in all) | 3 minutes 25° C. | 5 minutes 25° C. | 3 minutes 30° C. | 5 minutes 30° C. | 3 minutes 35° C. | 5 minutes 35° C. |
|---|---|---|---|---|---|---|
| Percent reflectance | 43.77 ± 1.18 | 32.73 ± 1.77 | 37.21 ± 1.05 | 25.28 ± 0.84 | 24.54 ± 1.22 | 18.10 ± 0.89 |

TABLE 23

Percent Reflectance at 450 nm for Chemical Indicators Including
ABTS Exposed to Various Decontamination Conditions

| | Conditions | |
|---|---|---|
| | 5 minutes full strength PAA 30° C. | 5 minutes 80% strength PAA 30° C. |
| Percent reflectance | 25.28 ± 0.84 | 28.06 ± 1.047 |

As can be seen in the data in Tables 22 and 23, there is a significant difference between reflectance readings at 5 minutes in 25° C., 30° C., and 35° C. There is also a significant difference between 3 and 5 minutes reflectance readings at each temperature, and there is a significant difference between reflectance readings at 5 minutes based on peracetic acid concentration at 30° C. These results suggest that the color of the disclosed chemical indicator has a dependence on PAA exposure time, temperature, and concentration. This chemical indicator could therefore be used to detect whether a high-level disinfection or sterilization process was deficient in any one of these three parameters.

Test Method for Examples 21-24

Coated samples were cut into 0.5×6 cm strips and suspended in temperature-controlled solution vessels. The samples were held stationary in the testing vessel submerged in solution for the specified time while the solution was stirred with a stir bar at 300 rpm. The exposure time and conditions are as follows: 1 minute exposure to water, 6 minutes exposure to peracetic acid ("PAA") solution (Medivators RAPICIDE PA, equivalent amounts of solutions A and B were used to make the specified dilution), followed by 2 minutes exposure to water. The strips were then dried with a paper towel and their reflectances at 450 nm were read against a white background with an X-Rite 500 Series Spectrodensitometer (X-Rite, Incorporated, Grand Rapids, Mich.). In these Examples, modifications were made to the polyurethane coating which allow the disclosed chemical indicators to distinguish effective from ineffective high-level disinfection or sterilization processes in high temperature/concentration cycle conditions (e.g., Steris) or higher concentration/lower temperature conditions (e.g., Olympus).

Example 21

A coating sample was prepared according to Formula 1 in Table 24 (percentages are given by weight). DSSA was stirred until dissolved in a solution of deionized water and ammonia. With constant stirring throughout, the following components were added to the DSSA solution in the order they are listed: AEAPS, NEOREZ R966, PZ-28. The mixed solution was coated onto a clear, Rhoplex primed 5 mil PET film using a slot die coater and the film was dried in a 130° C. oven for approximately 2 minutes. The coating was in the approximate range of 9-11 grams/square meter ("gsm") on the film.

TABLE 24

Coating Formulations for Examples 21-24

| | Example 21 | Example 22 | Example 23 | | | | | | | Example 24 | | | |
|---|---|---|---|---|---|---|---|---|---|---|---|---|---|
| Formula | 1 | 2 | 3 | 4 | 5 | 6 | 7 | 8 | 9 | 10 | 11 | 12 | 13 |
| DSSA | 1% | 1% | 1% | 1% | 1% | 1% | 1% | 1% | 1% | 0.80% | 1% | 0.80% | 1% |
| 30% Ammonia | 2% | 2% | 2% | — | — | — | — | — | — | — | — | — | — |
| TEA | — | — | — | 2% | 2% | 2% | 2% | 2% | 2% | 2% | 2% | 2% | 2% |
| NEOREZ R-9603 | — | — | — | 20% | — | — | — | — | — | 10% | 10% | 12% | 12% |
| NEOREZ R-650 | — | — | — | — | 20% | 20% | 20% | — | — | — | — | — | — |
| NEOREZ R-4000 | — | — | — | — | — | — | — | 20% | — | — | — | — | — |
| INCOREZ cs8057 | — | — | — | — | — | — | — | — | 20% | — | — | — | — |
| NEOREZ R-966 | 25% | 20% | 20% | — | — | — | — | — | — | 10% | 10% | 8% | 8% |
| AEAPS | 2% | — | — | — | — | — | — | — | — | — | — | — | — |
| PZ-28 | 1.25% | 2.00% | 3.00% | 1% | 1% | 2% | 3% | 1% | 1% | 2% | 2% | 2% | 2% |
| Deionized Water | 68.75% | 75% | 74% | 76% | 76% | 75% | 74% | 76% | 76% | 75.20% | 75% | 75.20% | 75% |

The coating was tested as described in the Test Method for Examples 21-24 above. Test conditions were as follows: 46° C. PAA solution temperature, 1820 ppm PAA. Results of testing are provided in Table 25.

TABLE 25

Percent Reflectance at 450 nm over Time

Reflectance at 450 nm

| 1 min | 2 min | 3 min | 4 min | 5 min | 6 min | 4-6 min difference |
|---|---|---|---|---|---|---|
| 33.305 | 18.73 | 16.045 | 16.86 | 16.47 | 17.5 | −0.64 |

As the data in Table 25 show, the reaction was over in about 2 minutes, and thus the formulation did not indicate a significant difference in reflectance between 4 and 6 minutes.

Example 22

The formulation as described in Example 21 was modified to adjust the aziridine crosslinker concentration. The percentage by weight for each component is given in Table 24 (see Formulas 2 and 3). DSSA was stirred until dissolved in a solution of deionized water and TEA. With constant stirring throughout, the following components were added to the DSSA solution in the order they are listed: NEOREZ R966, PZ-28. The mixed solution was coated onto a clear, Rhoplex primed 5 mil PET film using a #28 Mayer bar. The film coating was then dried in a 130° C. oven for approximately 2 minutes. The coating was tested as in the Test Method for Examples 21-24 above (46° C. PAA solution temperature, 1820 ppm PAA) and the reflectance measurements at 450 nm are provided in Table 26.

TABLE 26

Percent Reflectance at 450 nm over Time

Reflectance at 450 nm

| Formula | 1 min | 2 min | 3 min | 4 min | 5 min | 6 min | 4-6 min difference |
|---|---|---|---|---|---|---|---|
| 2 | 59.96 | 46.21 | 36.74 | 31.66 | 26.27 | 22.57 | 9.09 |
| 3 | 59.06 | 47.46 | 42.15 | 35.46 | 31.14 | 28.00 | 7.46 |

As the data in Table 26 show, the coatings of this Example show a more significant difference in percent reflectance between 4 and 6 minutes exposure time than those described in example 21 above.

Example 23

The formulation as described in Example 21 was modified with several different coating resins to test for their ability to slow the reaction of DSSA with PAA. The percentage by weight for each component in these new formulations is given in Table 24 (see formulas 4-9). DSSA was stirred until dissolved in a solution of deionized water and TEA. With constant stirring throughout, the following components were added to the DSSA solution in the order they are listed: the specified resin, PZ-28. The mixed solution was coated onto a clear, Rhoplex primed 5 mil PET film using a #28 Mayer bar. The film coating was then dried in a 130° C. oven for approximately 2 minutes. The coating was tested as in the Test Method for Examples 21-24 above (46° C. PAA solution temperature, 1820 ppm PAA), and the reflectance measurements at 450 nm are provided in Table 27.

TABLE 27

Percent Reflectance at 450 nm over Time

Reflectance at 450 nm

| Formula | 1 min | 2 min | 3 min | 4 min | 5 min | 6 min | 4-6 min difference |
|---|---|---|---|---|---|---|---|
| 4 | 70.25 | — | — | — | — | 64.28 | — |
| 5 | 7.745 | 0.22 | — | — | — | — | — |
| 6 | 43.34 | 19.385 | 7.525 | 3.18 | 2.065 | 1.75 | 1.43 |
| 7 | 49.825 | 25.81 | 13.95 | 9.48 | 8.095 | 7.945 | 1.535 |
| 8 | 55.04 | 35.14 | 24.76 | 18.455 | 17.99 | 12.575 | 5.88 |
| 9 | 55.025 | 36.27 | 21.445 | 13.125 | 11.095 | 7.595 | 5.53 |

As the data in Table 27 show, some resins, e.g., NEOREZ R-650, NEOREZ R-4000, INCOREZ cs8057, are able to significantly slow the reaction of DSSA with PAA so that a difference in percent reflectance may be seen over the entire 6 minutes time period. Some resins did not have ideal coating properties, so only a few were used for further evaluation described in Example 24.

Example 24

Portions of the formulations described in Examples 21 and 23 were combined and optimized for their ability to show a significant difference in percent reflectance at 450 nm between 4 and 6 minutes exposure to PAA. The percentage by weight for each component in these formulations is given in Table 24 (see formulas 10-13). DSSA was stirred until dissolved in a solution of deionized water and TEA. With constant stirring throughout, the following components were added to the DSSA solution in the order they are listed: the specified coating resins, PZ-28. The mixed solution was then coated onto a clear, Rhoplex primed 5 mil PET film using a slot die coater and the film was dried in a 130° C. oven for approximately 2 minutes. The coating was in the approximate range of 8-12 gsm on the film. The coating was tested as in the Test Method for Examples 21-24 above, and the reflectance measurements at 450 nm are provided in Table 28. Test conditions are provided in Table 28.

TABLE 28

Percent Reflectance at 450 nm over Time

46° C., 1820 ppm PAA

| Formula | 1 min | 2 min | 3 min | 4 min | 5 min | 6 min | 4-6 min difference |
|---|---|---|---|---|---|---|---|
| 10 | 63.51 | 51.25 | 39.585 | 26.97 | 19.155 | 14.305 | 12.665 |
| 11 | 59.15 | 42.47 | 26.075 | 16.64 | 10.575 | 6.225 | 10.415 |
| 12 | 64.31 | 53.845 | 45.935 | 34.225 | 28.605 | 23.615 | 10.61 |
| 13 | 56.08 | 35.305 | 21.545 | 14.25 | 8.07 | 4.88 | 9.37 |

| 40° C., 1820 ppm PAA | | | 46° C., 910 ppm PAA | | |
|---|---|---|---|---|---|
| Formula | 6 min | Difference from 46° C., 1820 ppm, 6 min | Formula | 6 min | Difference from 46° C., 1820 ppm, 6 min |
| 10 | 32.06 | 17.755 | 10 | 38.81 | 24.505 |
| 11 | 21.33 | 15.105 | 11 | 28.24 | 22.015 |
| 12 | 37.93 | 14.315 | 12 | 45.17 | 21.555 |
| 13 | 17.09 | 12.21 | 13 | 22.14 | 17.26 |

As the data in Table 28 demonstrate, the chemical indicators made with formulas 10-13 show a significant difference in percent reflectance when the time, temperature, or concentration are below the minimum recommended values of 46° C., 1820 ppm PAA, and 6 minutes exposure. These results suggest that the disclosed chemical indicators including may be used to distinguish between high-level disinfection or sterilization processes with adequate exposure time, PAA concentration, and temperature and decontamination processes where exposure time, PAA concentration, or temperature are not adequate.

Example 25

Olympus ACECIDE-C is used under different conditions than both Medivators RAPICIDE PA and Steris S40, even though all of these formulations use PAA as the high-level disinfectant. In this Example, two additional chemical indicator compositions (14 and 15) were made that contained a hydrophobic polyurethane (NEOREZ 9603). ACECIDE-C from Olympus was used at 2000 ppm of PAA with 7 minutes exposure time at 20° C. Formulation is shown below:

TABLE 29

Chemical Indicator Compositions

| Components | 14 % w/w | 15 % w/w |
|---|---|---|
| 4,4'-Diaminostilbene-2,2'-disulfonic Acid (DSSA) | 1.00 | 1.00 |
| Triethylamine | 2.00 | 2.00 |
| NEOREZ R9603 latex (34% solid) | 7.35 | 5.88 |
| NEOREZ R966 latex (32% solid) | 70.31 | 56.25 |
| TEGO Twin 4200 | 0.50 | 0.50 |
| PZ-28 | 2.00 | 2.00 |
| Deionized water | 16.83 | 32.37 |
| Total | 100.00 | 100.00 |

Each solution was coated on PET film as described above in Examples 21-24. The test method was similar to the Test Method for Examples 21-24, where the coated PET film was cut into strips and exposed to a solution providing 2000 ppm of PAA at 20° C. for four or seven minutes at the concentrations shown in Table 30. After exposure, the sample strips were dried and the percent reflectance at 450 nm was measured for each sample.

TABLE 30

Percent Reflectance at 450 nm for Various Times and PAA Concentrations

| | Conditions | | | | |
|---|---|---|---|---|---|
| | 2000 ppm PAA at 20° C. | | 20° C. for 7 minutes | | |
| | 4 min | 7 min | 1200 ppm PAA | 2000 ppm PAA | 3000 ppm PAA |
| 14 | 44.14 ± 2.28 | 27.99 ± 2.49 | 47.83 ± 1.26 | 28.02 ± 1.10 | 1.46 ± 0.33 |
| 15 | 33.37 ± 3.49 | 13.46 ± 2.19 | 35.42 ± 3.40 | 15.06 ± 1.57 | 0.38 ± 0.09 |
| Reference | 27.14 ± 2.31 | 12.55 ± 6.14 | 29.62 ± 0.33 | 12.16 ± 0.23 | 10.09 ± 0.18 |

As shown in Table 30, the chemical indicators prepared with formulations 14 and 15 show the time dependence of color development at a defined temperature (20° C.) and concentration (2000 ppm) as well as concentration dependence of color development at a defined temperature (20° C.) and time (7 minutes).

Example 26

A coating sample was prepared with the formulation in Table 31. DSSA was stirred until dissolved in a solution of deionized water and ammonia. With constant stirring throughout, the following components were added to the DSSA solution in the order they are listed: AEAPS, NEOREZ R966, PZ-28. The mixed solution was then coated onto a clear, Rhoplex primed 5 mil PET film using a slot die coater and the film was dried in a 129° C. oven for approximately 2 minutes. The coat weight was in the approximate range of 10-14 grams/square meter ("gsm") on the film.

TABLE 31

Chemical Indicator Compositions

| Components | w/w % |
|---|---|
| 4,4'-Diaminostilbene-2,2'-disulfonic Acid (DSSA) | 1.00 |
| Ammonium hydroxide (30% aqueous) | 3.00 |
| Deionized water | 14.87 |
| N-[3-(Trimethoxysilyl)propyl]ethylenediamine (AEAPS) | 2.00 |
| NEOREZ R966 latex (32% solid) | 78.13 |
| PZ-28 | 1.00 |
| Total | 100.00 |

The coating samples were tested in a cycle designed to mimic the standard conditions of an automated endoscope reprocessing machine, namely the exposure time, exposure temperature, concentration of peracetic acid high level disinfectant, solution flow rate, and line pressure. The parameters of time, temperature, peracetic acid concentration, and flow rate were varied individually to show that the coating's color change is dependent on each of the aforementioned parameters. Samples of 5 mil PET coated with the formulation in table 28 were exposed to the following cycle conditions (all times are min:sec): 2:00 water rinse, 3:09 0.5% INTERCEPT detergent wash, 3:06 water rinse, peracetic acid exposure (variable times listed in table below), 1:30 water rinse, 2:30 final water rinse, rinse 70% isopropyl alcohol <0:05. The colorimetric endpoint when time, temperature, peracetic acid concentration, or flow rate was varied is shown in Table 32. After the cycle, the reflectance of the coating sample at 450 nm and 550 nm were read. The reflectance at 450 nm was divided by the reflectance at 550 nm in order to determine the colorimetric endpoint.

TABLE 32

Colorimetric Endpoint for Minimum Effective Decontamination Conditions and Various Failure Modes

| Cycle | Minimum Effective Conditions | Contact Time Failure | Temperature Failure | Concentration Failure | Flow Failure |
|---|---|---|---|---|---|
| Peracetic Acid Exposure Time (min:sec) | 5:00 | 3:00 | 5:00 | 5:00 | 5:00 |
| Temperature of Solutions (° C.) | 30 | 30 | 23 | 30 | 30 |
| Peracetic Acid Concentration (ppm) | 850 | 850 | 850 | 550 | 850 |
| Active Flow? | Yes | Yes | Yes | Yes | No - flow interrupted during peracetic acid exposure |
| Colorimetric Endpoint Immediately After Cycle | 0.674 | 0.807 | 0.812 | 0.807 | 0.795 |
| Colormetric Endpoint Approximately 1 Hour After Cycle | 0.706 | 0.815 | 0.816 | 0.821 | 0.808 |

Table 32 shows the conditions of each test and the ratio of the reflectance readings at 450 nm and 550 nm of the coating after the cycle. The colorimetric endpoint of the samples was determined again an hour later. The results show that the color change over time is minimal and that there is still enough difference after 1 hour to determine whether each sample was exposed to passing or failing decontamination conditions.

All cited references, patents, and patent applications in the above application for letters patent are herein incorporated by reference in their entirety in a consistent manner. In the event of inconsistencies or contradictions between portions of the incorporated references and this application, the information in the preceding description shall control. The preceding description, given in order to enable one of ordinary skill in the art to practice the claimed disclosure, is not to be construed as limiting the scope of the disclosure, which is defined by the claims and all equivalents thereto.

What is claimed is:

1. A peracetic acid decontamination chemical indicator comprising:
   a substrate; and
   an indicator composition disposed thereon,
   wherein the indicator composition comprises a colorant that reacts to change color when exposed to a peracetic acid solution but does not change color when exposed to a hydrogen peroxide solution, an acidified hydrogen peroxide solution, or an acetic acid solution, wherein the colorant includes a moiety selected from the group consisting of an azido, a benzothiazole, a benzoxazole, an indole, a pyrazole, a pyridine, a stilbene, a styrene, a sugar, and combinations thereof, and wherein the indicator composition does not include a transition metal salt or a halogen source;
   wherein the substrate is a selected from the group consisting of a nylon membrane, a silica particle, a polyethylene terephthalate film, and combinations thereof;
   wherein the nylon membrane is selected from the group consisting of an uncharged nylon membrane, a positively charged nylon membrane, a negatively charged nylon membrane, and combinations thereof;
   wherein the silica particle is selected from the group consisting of a positively charged silica particle, a negatively charged silica particle, and combinations thereof;
   with the proviso that when the substrate comprises the polyethylene terephthalate film, the indicator composition further comprises a binder.

2. The peracetic acid decontamination chemical indicator of claim 1, wherein the indicator composition comprises the binder.

3. The peracetic acid decontamination indicator of claim 2, wherein the binder comprises a polymer latex.

4. The peracetic acid decontamination chemical indicator of claim 1, wherein the indicator composition further comprises a base.

5. The peracetic acid decontamination chemical indicator of claim 4, wherein the base is selected from the group consisting of an inorganic base, an organic base, an amine-derivatized silane, and combinations thereof.

6. The peracetic acid decontamination chemical indicator of claim 1, wherein the colorant does not include a naphthalene moiety or an anthraquinone moiety.

7. The peracetic acid decontamination chemical indicator of claim 1, wherein the colorant is selected from the group consisting of 5-bromo-4-chloro-3-indolyl beta-D-galactopyranoside, 4,4'-diamino-2,2'-stilbenedisulfonic acid, 4-aminoantipyrine, 2-[4-(dimethylamino)styryl]-1-methylpyridinium iodide, 2,2'-azino-bis(3-ethylbenzothiazoline-6-sulfonic acid) diammonium salt, azidoaniline, trans-4-[4-(dimethylamino)styryl]-1-methylpyridinium iodide, tetramethylbenzidine hydrochloride, and combinations thereof.

8. A method of monitoring a peracetic acid decontamination process, the method comprising:
   exposing an article to be disinfected and the peracetic acid decontamination indicator of claim 1 to a sterilant comprising peracetic acid during a decontamination process, wherein a predetermined decontamination exposure criterion exists for contacting the article with the sterilant;
   measuring a color change of the exposed peracetic acid decontamination indicator, wherein the color change is predictive of the predetermined disinfectant exposure criterion; and determining whether the predetermined disinfectant exposure criterion has been achieved.

9. The method of claim 8, wherein the color change is dependent upon a decontamination process condition selected from the group consisting of concentration of peracetic acid in the sterilant liquid, exposure temperature, exposure time, the rate of sterilant liquid flow across the decontamination indicator, and combinations thereof.

10. The method of claim 8, wherein the concentration of peracetic acid in the sterilant liquid is at least 550 ppm during the decontamination process.

11. The method of claim 8, wherein the temperature of the sterilant liquid is 20° C.-50° C. during the decontamination process.

12. The method of claim 8, wherein the exposure time of the decontamination indicator to the sterilant liquid is at least 1 minute.

13. The method of claim 8, wherein the rate of sterilant liquid flow across the decontamination indicator is at least 400 mL per minute.

14. The method of any claim 8, wherein detecting the color change of the decontamination indicator comprises detecting a change in percent optical reflectance of the decontamination indicator at 375 nm-800 nm.

15. A decontamination monitoring device comprising the peracetic acid decontamination indicator of claim 1.

16. The peracetic acid decontamination chemical indicator of claim 2, wherein the binder is a water-soluble polymeric binder.

* * * * *